US006015710A

United States Patent [19]
Shay et al.

[11] Patent Number: 6,015,710
[45] Date of Patent: Jan. 18, 2000

[54] MODULATION OF MAMMALIAN TELOMERASE BY PEPTIDE NUCLEIC ACIDS

[75] Inventors: Jerry W. Shay, Dallas; Woodring E. Wright, Arlington, both of Tex.; Mieczyslaw A. Piatyszek, San Jose, Calif.; David R. Corey; James C. Norton, both of Dallas, Tex.

[73] Assignee: The University of Texas System, Austin, Tex.

[21] Appl. No.: 08/630,019

[22] Filed: Apr. 9, 1996

[51] Int. Cl.[7] .............................. C12N 5/16; A61K 38/08; A61K 38/16; C07H 21/00
[52] U.S. Cl. .......................... 435/375; 530/326; 530/327; 530/328; 536/24.5
[58] Field of Search ................................ 435/6, 7.1, 7.21, 435/325, 375; 514/12, 13, 14, 15, 16, 17, 44; 530/300, 324, 325, 326, 327, 328, 329; 536/22.1, 23.1, 24.3, 24.31, 24.5; 424/450

[56] References Cited

U.S. PATENT DOCUMENTS

| | | | |
|---|---|---|---|
| 5,489,508 | 2/1996 | West et al. | 435/6 |
| 5,583,016 | 12/1996 | Villeponteau et al. | 435/91.3 |
| 5,643,890 | 7/1997 | Iversen et al. | 514/44 |
| 5,700,922 | 12/1997 | Cook | 536/23.1 |
| 5,776,679 | 7/1998 | Villeponeau et al. | 435/6 |

FOREIGN PATENT DOCUMENTS

| | | |
|---|---|---|
| 95/04068 | 2/1995 | WIPO . |
| 96/01614 | 1/1996 | WIPO . |
| 96/01835 | 1/1996 | WIPO . |
| 97/14026 | 4/1997 | WIPO . |

OTHER PUBLICATIONS

Antisense '97: A Roundtable on the State of the Industry. Nature Biotechnology 15: 519–524, Jun. 1997.
Gewirtz et al. Facilitating Oligonucleotide Delivery: Helping Antisense Deliver on its Promise. Proc. Natl. Acad. Sci. USA 93: 3161–3163, Apr. 1996.
Gura. Antisense has Growing Pains. Science 270: 575–577, Oct. 1995.
Nielsen et al. Peptide nucleic Acids (PNAs): Potential Anti-–sense and Anti–gene Agents. Anti–Cancer Drug Deign 8: 53–63, 1993.
Rojanasakul. Antisense Oligonucleotide Therapeutics: Drug Delivery and Targeting. Adv. Delivery Rev. 18: 115–131, 1996.
J.C. Norton, Jr., Peptides nucleic acids; characterization of their hybridization to deplex DNA and inhibitory effects on human telomerase activity (gene sequence), *Dissertations Abstracts Int.*, 57:4 p 2414, B 1996.
J.C. Norton, et al., Inhibition of human telomerase activity by peptide nucleic acids, *Chemical Abstracts* 24:23, Jun. 3, 1996.
Demidov, Vadim V. et al., "Stability of peptide nucleic acids in human serum and cellular extracts", *Biochemical Pharmacology*, 48:6 pp. 1310–1313 (1994).
Dueholm, Kim L. et al., "Synthesis of Peptide Nucleic Acid Monomers Containing the Four Natural Nucleobases: Thymine, Cytosine, Adenine, and Guanine and Their Oligomerization", *J. Org. Chem.*, 59:5767–5773 (1994).
Egholm, Michael et al., "PNA hybridizes to complementary oligonucleotides obeying the Watson–Crick hydrogen–bonding rules", *Nature*, 365:566–568 (1993).
Feng, Junli et al., "The RNA Component of Human Telomerase", *Science*, 269:1236–1241 (1995).
Hanvey, Jeffrey C. et al., "Antisense and Antigene Properties of Peptide Nucleic Acids", *Science*, 258:1481–1485 (1992).
Nielsen, Peter E. et al., "Sequence–Selective Recognition of DNA by Strand Displacement with a Thymine–Substituted Polyamide", *Science*, 254:1497–1500 (1991).
Shippen–Lentz, Dorothy and Blackburn, Elizabeth H., "Functional Evidence for an RNA Template in Telomerase", *Science*, 247:546–552 (1990).
Thompson, Stephen A. et al., "Fmoc Mediated Synthesis of Peptide Nucleic Acids", *Tetrahedron*, 51:22 pp. 6179–6194 (1995).
Wittung, Pernilla et al., "Phospholipid membrane permeability of peptide nucleic acid", *FEBS Letters*, 365:27–29 (1995).
Norton, James C. et al., "Inhibition of human telomerase activity by peptide nucleic acid" *Nature Biotechnology*, 14:615–619 (1996).

*Primary Examiner*—Nancy Degen
*Assistant Examiner*—Thomas G. Larson
*Attorney, Agent, or Firm*—Amy Collins; Annette S. Parent; John R. Storella

[57] ABSTRACT

The invention relates to peptide nucleic acids that modulate telomerase activity in mammalian cells.

8 Claims, 7 Drawing Sheets

ESSENTIALLY NON-REVERSIBLE

MODULATION OF MAMMALIAN TELOMERASE BY PEPTIDE NUCLEIC ACIDS

FIELD OF THE INVENTION

The invention relates to synthetic non-naturally occurring oligodeoxyribonucleotides and/or non-naturally occurring oligoribonucleotides and their utilization in modulating the enzymatic activity, stability, and other properties of mammalian telomerase, and methods for using such oligonucleotides to purify mammalian telomerase proteins, to detect telomerase polynucleotide sequences for diagnostic evaluation, and to treat telomerase-related disease conditions.

BACKGROUND

Non-Phosphodiester Polynucleotide Analogs

DNA consists of covalently linked units, each composed of a nucleobase (adenine, cytosine, guanine, or thymine) attached to a pentose sugar (deoxyribose) via a glycosidic linkage, with a phosphate ester (phosphodiester) linking successive sugar rings. Numerous types of DNA analogs have been synthesized, with most variations typically having a modification or replacement of the phosphodiester backbone.

Examples of non-phosphodiester polynucleotide analogs having a modified phosphate backbone include: methylphosphonates, phosphorothioates, phosphoramidites, phosphorodithioates, phosphorotriesters, and boranophosphates. An alternative approach is the development of structural mimetics of the phosphodiester linkage, generally with the objective of providing a backbone linkage that is charge neutral (to increase the stability of DNA hybrid complexes), relatively hydrophobic (to increase cellular uptake), and achiral. Examples of non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, glycinylamides, and others.

In addition to replacing the phosphodiester linkage, alternative approaches have replaced the entire (deoxy)ribose-phosphate backbone, retaining just the nucleobases. One of these approaches replaces the entire (deoxy)ribose-phosphate backbone with a peptide-like backbone, generating a so-called "peptide nucleic acid", "polyamide nucleic acid", or simply "PNA" (Nielsen et al. (1991) Science 254: 1497; Nielsen et al. (1994) Bioconj. Chem. 5: 3; Leijon et al. (1994) Biochemistry 33: 9820; Huang et al. (1991) J. Org. Chem. 56: 6007; Egholm et al. (1993) Nature 365: 556; Buchardt et al. (1993) Trends Biotechnol. 11; 384; Nielsen PE (1995) Rev Biophys Biomol Struct 24: 167;Agrawal et al. (1995) Curr Opin Biotechnol. 6: 12; Nielsen et al. (1993) Anticancer Drug Res. 8: 53; Cook PD (1991) Anticancer Drug Des. 6: 585, incorporated herein by reference). PNAs have an achiral, noncharged backbone, as exemplified by a backbone composed of N-(2-aminoethyl)glycine units, which is a suitable structural mimic of DNA. Hybrids between such a PNA and complementary sequence DNA or RNA are reported to exhibit higher thermal stability per base pair than DNA:DNA or RNA:RNA duplexes (Wittung et al. Nature 368: 561).

PNAs have been reported to have many interesting properties. Binding of PNA to double-stranded DNA occurs by strand invasion via formation of a D-loop strand displacement complexes (Egholm et al. (1993) Nature 365: 556) that have unique biological properties, including the capacity to serve as artificial transcription promoters in some contexts (Mollegaard et al. (1994) Proc. Natl. Acad. Sci. (U.S.A.) 91: 3892). PNAs have been shown to bind to DNA and RNA in a sequence-dependent manner (Brown et al. (1994) Science 265: 777; Egholm et al. (1993) op.cit), and exhibit superior base pair mismatch discrimination in PNA/DNA hybrids than do DNA/DNA duplexes (Orum et al. (1993) Nucleic Acids Res 21: 5332).

PNAs have been used to target the single strand-specific nuclease S1 to a PNA/DNA hybrid formed via strand invasion, making S1 nuclease act like a pseudo restriction enzyme (Demidov et al. (1993) Nucleic Acids Res 21: 2103). Alternatively, complementary PNAs have been used to block sequence-specific DNA restriction enzyme cleavage of dsDNA plasmids (Nielsen et al. (1993) Nucleic Acids Res 21: 197). PNAs have been used to arrest transcription elongation by targeting a complementary sequence PNA to the template DNA strand (Nielsen et al. (1994) Gene 149: 139). PNA strand invasion has also been shown to inhibit transcriptional activation by the transcription factor NF-κB by blocking its interaction with 5' regulatory sequences to which it normally binds (Vickers et al. (1995) Nucleic Acids Res 23: 3003).

Interaction of certain DNA-binding ligands with PNA/DNA 1:5 hybrids has also been reported (Wittung et al. (1994) Nucleic Acids Res 22: 5371).

The antisense and antigene properties of PNAs have been reported (Bonham et al. (1995) Nucleic Acids Res 23: 1197; Hanvey et al. (1992) Science 258: 1481; Nielsen et al. (1993) AntiCancer Drug Des 8: 53). A vector-mediated delivery method for introducing PNAs through phospholipid membranes and through the blood-brain barrier have been reported (Pardridge et al. (1995) Proc. Natl. Acad. Sci. (U.S.A.) 92: 5592; Wittung et al. (1995) FEBS Lett 375: 27). Orum et al. (1995) Biotechniques 19: 472 report a method for sequence-specific purification of nucleic acids by PNA-controlled hybrid selection.

Telomerase and Telomerase-Related Proteins

The DNA at the ends or telomeres of the chromosomes of eukaryotes usually consists of tandemly repeated simple sequences. Telomerase is a ribonucleoprotein enzyme that synthesizes one strand of the telomeric DNA using as a template a sequence contained within the RNA component of the enzyme. See Blackburn, 1992, Annu. Rev. Biochem. 61:113–129, incorporated herein by reference. The RNA component of human telomerase has been reported (Feng et al. (1995) Science 269: 1267, incorporated herein by reference, and the PCT publication infra).

There is a great need for more information about human telomerase and for agents that can modulate telomerase activity, either in vitro or in vivo. Despite the seemingly simple nature of the repeat units of telomeric DNA, scientists have long known that telomeres have an important biological role in maintaining chromosome structure and function. More recently, evidence consistent with a loss of telomeric DNA acting as a trigger of cellular senescence and aging indicates that regulation of telomerase may have important biological implications. See Harley, 1991, Mutation Research 256:271–282, incorporated herein by reference.

Methods for detecting telomerase activity, as well as for identifying compounds that regulate or affect telomerase activity, together with methods for therapy and diagnosis of cellular senescence and immortalization by controlling telomere length and telomerase activity, have also been described. See PCT patent publication Nos. 95/13381, published May 18, 1995; 95/13382, published May 18, 1995; and 93/23572, published Nov. 25, 1993, each of which is incorporated herein by reference.

Significant improvements to and new opportunities for telomerase-mediated therapies and telomerase assays and screening methods could be realized if encoding polynucleotides (mRNA or cDNA) of protein components involved in mammalian telomerase function could be selectively modified such that the telomerase enzymatic activity was altered.

The present invention meets these and other needs and provides such improvements and opportunities.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference, whether specifically noted as such or not.

SUMMARY OF THE INVENTION

The present invention relates to PNAs comprising a PNA sequence substantially identical to or substantially complementary to a mammalian telomerase RNA component sequence that are capable of interacting with telomerase and modifying its catalytic activity. Typically, the PNA comprises a nucleobase sequence that is substantially identical or substantially complementary to the template repeat sequence of the mammalian telomerase RNA component, preferably a human telomerase RNA component (hTR) template region. Often, the PNA comprises a nucleobase sequence that is identical or complementary to at least 6 nucleotides of the template repeat sequence of the mammalian telomerase RNA component, preferably complementary to at least 9, 10, or 11 nucleotides of the template repeat sequence, respectively, and more preferably further comprises sequences identical or complementary to sequences adjacent to the template repeat sequence, and have a unit of length of 15 units or less. Often the PNA comprises a nucleobase sequence that is complementary to at least 6 consecutive nucleotides of the template sequence, preferably the PNA comprises a nucleobase sequence that is complementary to at least 9 to 11 consecutive nucleotides of the template region, and more preferably further comprises sequences identical or complementary to sequences adjacent to the template repeat sequence, and have a unit of length of 15 units or less.

In an aspect, the invention provides a peptide nucleic acid polymer comprising:

six to twenty-five polymerized PNA monomer units linked by peptide bonds, wherein said at least six PNA monomer units comprise a nucleobase sequence having a sequence complementary to at least six contiguous nucleotides of a mammalian telomerase template region. In an embodiment, the peptide nucleic acid polymer further comprises at least one amino-terminal amine or amino acid and at least one carboxy-terminal amino acid or carboxylate. It is typical for the peptide nucleic acid polymer to comprises a sequence of PNA monomer units having a nucleobase sequence complementary to at least six to twenty three contiguous nucleotides of a mammalian telomerase template region. In an aspect, the amino-terminus of the PNA comprises an N-linked substitutent, such as acetyl, benzoic acid, retenoic acid, cholesterol derivative, and the like. The amino terminus can alternatively or in addition comprise one or more amino or imino acids (e.g., Pro, Tyr, Phe, Gly, Lys, Ser, Cys), generally linked vis peptide bond to the amine nitrogen of the PNA sequence, and/or a linked polynucleotide sequence. In an aspect, the carboxy-terminus of the PNA comprises a polypeptide, amino acid, nucleotide, or polynucleotide, generally linked to the carboxylate via an ester or other carbonyl bond (e.g., peptide bond for linked amino acid). As an example, the carboxy-terminus can comprise a moiety having a thiol group suitable for forming disulfide, thioether, or thioester linkages, such as with other thiol-containing molecules (e.g., a Cys- containing polypeptide), nucleotides capable of forming thioether or thioester linkages, and the like, including non-peptide, non-nucleotide moieties. In an aspect, the PNA comprises a linked hydrophobic moiety (e.g., a cholesterol derivative or fatty acyl chain) for enhanced cell uptake and/or liposomal formulation.

In am embodiment, the peptide nucleic acid polymer comprises polymerized PNA monomer units having a nucleobase sequence according to one of the following formulae:

—TTAGGG— (SEQ ID NO:1)

—TAGGGT— (SEQ ID NO:2)

—AGGGTT— (SEQ ID NO:3)

—GGGTTA— (SEQ ID NO:4)

—GGTTAG— (SEQ ID NO:5)

—GTTAGG— (SEQ ID NO:6)

wherein each PNA nucleobase sequence can be extended by $N_x$ PNA nucleobases at the amino terminal end and $N_y$ PNA nucleobases at the carboxy terminal end and wherein each PNA nucleobase, N, is each independently selected from uridine, thymine, adenine, guanine, inosine, cytosine, and any amino acid, and x is 0–50 and y is 0–50, and wherein the nucleobase thymine can be replaced by the nucleobase uridine, at some or all occurrences of T. In an embodiment, x is 0–17, y is 0–17, with the proviso that the sum of x and y is 0–17. For exemplification and not limitation, in one embodiment $N_x$ is GGTC (SEQ ID NO:21), $N_y$ is ACTG (SEQ ID NO:22) and the resultant PNA sequence is —GGTCTTAGGGACTG— (SEQ ID NO:7), that can, if desired, comprise amino-terminal and/or carboxy-terminal extensions of amino acids, nucleotides, polynucleotides, cholesterol derivatives, retenoic acid, benzoic acids, acetyl, formyl, or other acyl substitutents, or any non-interfering N-linked, O-linked, or C-linked substituent(s).

The invention provides methods for treating a condition associated with the telomerase activity within a cell or group of cells by contacting the cell(s) with a therapeutically effective amount of a telomerase modulating PNA that alters telomerase activity in that cell. Such PNAs include PNAs having a corresponding or complementary sequence to the telomerase RNA component, PNA-based ribozymes, and other PNAs capable of modulating mammalian telomerase gene activity, such as for human gene therapy.

In a related aspect, the invention provides pharmaceutical compositions comprising these therapeutic telomerase-modulating PNA species, alone, in combination with each other or other therapeutic agents, and/or together with a pharmaceutically acceptable carrier or salt, which may include formulation in a lipofection complex, liposome, or immunoliposome for targeted delivery of the therapeutic PNA agent. The invention also provides combinations of such telomerase-modulating therapeutic PNAs with other pharmaceuticals, such as antineoplastic agents and other cytotoxic or cytostatic agents; antifungal agents (e.g., for treatment of AIDS patients); nucleotides, nucleosides, and analogs thereof; and other pharmaceutical agents suitable for treating disease conditions such as neoplasia, hyperplasia, HIV-infection/AIDS and associated pathologies, and other diseases characterized by abnormal telomere metabolism or telomerase activity. The methods can comprise the use of a derivatized PNA capable of specifically hybridizing to a telomerase RNA component in a mammalian telomerase, wherein the derivatized PNA is delivered into mammalian cells having telomerase activity and inhibits telomerase activity by localizing to telomerase RNA component or telomerase protein component, or telomeric sequences of a chromosome, and thereby inactivating or inhibiting telomerase activity.

The invention also provides PNA therapeutic agents that inhibit neoplasia or apoptosis by modulating telomerase function by mimicing or inhibiting telomerase RNA component; such therapeutic PNAs can be used as pharmaceuticals as well as commercial laboratory reagents. Such pharmaceuticals will be used to treat a variety of human and veterinary diseases, such as: neoplasia, hyperplasia, neurodegenerative diseases, aging, AIDS, fungal infection, and the like. In an embodiment, the PNA comprises a PNA nucleobase sequence capable of inhibiting telomerase by mimicing and/or binding to (hybridizing to) a telomerase RNA component sequence, or alternatively the PNA can serve as an enzymatically inactive telomerase RNA component that can competitively inhibit formation of functional telomerase holoenzyme. In one aspect, the PNAs of the invention can be used for molecular diagnostic embodiments, such as the use of detectable, i.e., labeled, PNAs to serve as hybridization probes to detect and/or quantitate polynucleotides (e.g., MRNA or genomic DNA) having the human hTR sequence; the PNA probes are also used for forensic identification of individuals, such as for paternity testing or identification of criminal suspects or unknown decedents based on their hTR gene RFLP pattern.

The invention provides a method for attenuating mammalian telomerase activity, comprising administering an effective amount of a PNA comprising a nucleobase sequence complementary to a nucleotide sequence of a mammalian telomerase RNA component, generally comprising at least six consecutive nucleobases complementary to the RNA template of telomerase. In an aspect, the PNA comprises the nucleobase sequence NH2-GGTTAG-COOH (SEQ ID NO:5) or NH2-GGUUAG-COOH (SEQ ID NO:19). In a related aspect, the PNA comprises a nucleobase sequence selected from: NH2-TAGGGTTAG-COOH (SEQ ID NO:20); NH2-TTAGGGTTAG-COOH (SEQ ID NO:9); NH2-GTTAGGGTTAG-COOH (SEQ ID NO:9); NH2-AGTTAGGGTTAG-COOH (SEQ ID NO:10); NH2-CAGTTAGGGTTAG-COOH (SEQ ID NO:11); NH2-CTCAGTTAGGGTTAG-COOH (SEQ ID NO:12); NH2-CCCTTCTCAGTTAGGGTTAG-COOH (SEQ ID NO:13); NH2-TAGGGTTAGAC-COOH (SEQ ID NO:14); NH2-GTTAGGGTTAGAC-COOH (SEQ ID NO:15); NH2-GGGTTAGACAA-COOH (SEQ ID NO:16); NH2-TAGGGTTAGACAA-COOH (SEQ ID NO:17); or NH2-GTTAGGGTTAGACAA-COOH (SEQ ID NO:18), or these sequences wherein the nucleobase thymine is replaced by the nucleobase uridine, at some or all occurrences of T. In an aspect, the PNA comprises additional terminal nucleobases and/or amino or imino acid residues (e.g., Lys, Tyr, etc.), and may comprise chemical modifications (e.g., biotinylation, methylation, iodination) or extensions, often at the amino-terminus or carboxyl-terminus. For example and not limitation, PNAs of the present invention can be of the following formulae:

| | |
|---|---|
| NH2-TTAGGG-COOH | (SEQ ID NO:1) |
| NH2-TAGGGT-COOH | (SEQ ID NO:2) |
| NH2-AGGGTT-COOH | (SEQ ID NO:3) |
| NH2-GGGTTA-COOH | (SEQ ID NO:4) |
| NH2-GGTTAG-COOH | (SEQ ID NO:5) |
| NH2-GTTAGG-COOH | (SEQ ID NO:6) | wherein each PNA nucleobase sequence can be extended by $N_x$ PNA nucleobases at the amino terminal end and $N_y$ PNA nucleobases at the carboxy terminal end and wherein each nucleobase, N, is each independently selected from uridine, thymine, adenine, guanine, inosine, cytosine, and any amino acid, and x is 0–1000, preferably 1–13 and y is 0–1000, preferably 1–13, often 1–4, such that for example $N_x$ can be NH2-CCCTTCTCAGTTAG-COOH (SEQ ID NO:25) and $N_y$ can be NH2-ACAA-COOH (SEQ ID NO:44). In each of these sequences, the nucleobase thymine can be replaced by the nucleobase uridine, at some or all occurrences of T. In an aspect of the invention, $N_x$ and/or $N_y$ are nucleobase sequences that are complementary to all or a portion of the human telomerase RNA component repeat region and its adjacent sequences. A preferred example of the human hTR repeat region and its adjacent sequences is NH2-UUUGUCUAACCCUAACUBAGAAGGG-COOH (SEQ ID NO:26), although allelic variants can exist within the human population, among other sequence variants.

Additional illustrative examples of PNA sequences of the invention include, but are not limited to:

| | |
|---|---|
| NH2-GTATTAGGG-COOH | (SEQ ID NO:27) |
| NH2-CAGTATTAGGG-COOH | (SEQ ID NO:28) |
| NH2-CTCAGTATTAGGG-COOH | (SEQ ID NO:29) | wherein each PNA nucleobase sequence can be extended by $N_x$ PNA nucleobases at the amino terminal end and $N_y$ PNA nucleobases at the carboxy terminal end and wherein each nucleobase, N, is independently selected from uridine, thymine, adenine, guanine, inosine, cytosine, and any amino acid, and x is 0–1000, preferably 1–50 and y is 0– 1000, preferably 1–50, often 1–4, such that for example $N_y$ can be NH2-ACAA-COOH (SEQ ID NO:44). In each of these sequences, the nucleobase thymine can be replaced by the nucleobase uridine, at some or all occurrences of T. In an aspect of the invention, $N_x$ and/or $N_y$ are nucleobase sequences that are complementary to all or a portion of the human telomerase RNA component repeat region or its adjacent sequences.

Other suitable nucleobase sequences and variations are evident to the skilled artisan in view of the teachings of the specification and experimental examples, see, e.g., Table 1, infra. Each PNA comprising a selected nucleobase sequence variant can be conveniently and routinely assayed to determine the exact level of activity, such as the $IC_{50}$ value using the assay methods taught in the experimental examples, and PNA species having a desired level of activity at inhibiting telomerase can be chosen for further use and formulation.

The invention also comprises a mismatch sequence PNA which typically comprises a single nucleobase mismatch relative to the naturally-occurring template sequence or its complement, and may comprise two nucleotide mismatches in the template sequence, either as adjacent mismatched nucleobases or wherein the mismatched nucleobases are separated by one or more matched (complementary) nucleobases.

In an aspect, the invention provides methods for purifying the protein components of human telomerase. In such an aspect, a capture PNA comprising a nucleobase sequence complementary to the human hTR or other hTR, and optionally a linked nucleobase sequence which is optionally not present in the human or other hTR or complementary to the human hTR sequence is retreivably labeled (e.g., biotinylated, terminal amino acid sequence epitope tag) and contacted with a sample having human or other telomerase, resulting in hybridization to the telomerase RNA component (hTR) of the telomerase holoenzyme forming a PNA:telomerase holoenzyme complex; the PNA:telomerase holoenzyme complex is immobilized or captured by retrieving the retreivably labeled PNA (e.g., with streptavidin if the PNA is biotinylated, or by specific antibody if the PNA is epitope tagged), thereby selectively isolating telomerase holoenzyme. If desired, the captured (immobilized) telomerase can be released from the PNA:telomerase holoenzyme complex by contacting the complex with a release PNA comprising a nucleobase sequence complementary to the nucleobase sequence of the capture PNA, forming a duplex with the capture PNA and thereby displacing the capture PNA from the telomerase holoenzyme. In a preferred aspect, the capture PNA lacks a sequence complementary to the portions of the hTR necessary for binding to telomerase proteins.

In an embodiment, candidate telomerase modulating PNA nucleobase sequences are identified by their ability to produce a statistically significant increase or decrease in enzymatic activity of mammalian telomerase, in either purified or unpurified form. A pool of PNA species comprising variant sequences having 1, 2, 3, 4, 5, or 6 mismatches as compared to a naturally-occurring mammalian telomerase RNA component or its complement are screened, typically over a range of varying concentrations, for their ability to produce a statistically significant increase or decrease in enzymatic activity of a mammalian telomerase (recombinant or naturally-occurring in purified or unpurified form). In similar fashion, the ability of a PNA to capture telomerase for purification can be ascertained and, if desired, quantified. In a variation, a pool of PNA species comprising a sequence of at least 6 nucleobases having no mismatches relative to a naturally-occurring mammalian telomerase RNA component or its complement are screened, typically over a range of varying concentrations, for their ability to produce a statistically significant increase or decrease in enzymatic activity of a mammalian telomerase comprising a purified telomerase protein component and a telomerase RNA component. The PNA species can comprise additional N-terminal and/or C-terminal extensions, such as additional PNA nucleobase units and/or amino or imino acids; such terminal additions generally are less than 10,000 units and are preferably substantially non-interfering (i.e., the presence of the addition does not significantly interfere with function of the PNA).

An aspect of the invention provides a composition comprising a peptide nucleic acid polymer capable of modulating telomerase activity in a cell and an excipient or delivery vehicle. In an embodiment, the delivery vehicle is a liposome formulation.

Other features and advantages of the invention will be apparent from the following description of the drawings, preferred embodiments of the invention, the examples, and the claims.

DETAILED DESCRIPTION

Definitions

Figure 1C:
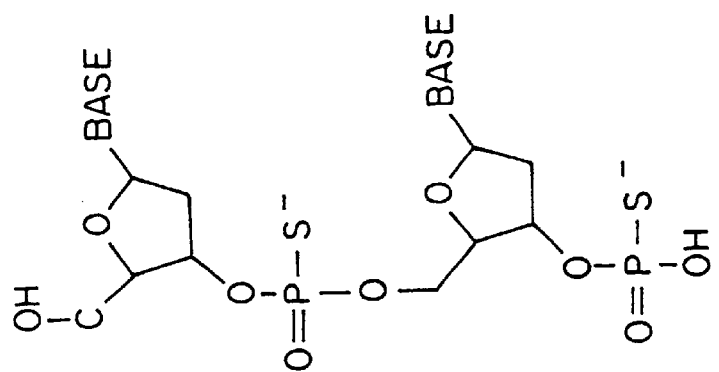
FIG. 1. Chemical structure of DNA (Panel A), PNA (Panel B), and PS (Panel C).

The term "telomerase RNA component polynucleotide" as used herein refers to a polynucleotide of at least 20 nucleotides wherein the polynucleotide comprises a segment of at least 20 nucleotides which: are at least 85 percent identical in a nucleotide sequence to a naturally-occurring mammalian telomerase RNA component or a gene encoding such a component, typically a primate telomerase RNA component such as a human or monkey telomerase RNA component. Some telomerase RNA component polynucleotides having sequence variations as compared to a naturally-occurring telomerase RNA component or a polynucleotide comprising a sequence complementary thereto can be suitable as hybridization probes, PCR primers, LCR amplimers, mismatch RNA components, and the like. A preferred RNA component is a full length mature human telomerase RNA component (hTR) (see, Feng et al. (1995) *Science* 269: 1267; PCT patent publication Nos. 95/13381, published May 18, 1995; 95/13382, published May 18, 1995; and 93/23572, published Nov. 25, 1993; PCT patent publication No. 96/01835, published Jan. 25, 1996; PCT patent publication No. 96/01614, published Jan. 25, 1996; and commonly-assigned U.S. Ser. Nos. 08/521,634 filed Aug. 31, 1995, 08/330,123 filed Oct. 27, 1994, now U.S. Pat. No. 5,583,016, 08/472,802 filed Jun. 7, 1995, 08/482,115 filed Jun. 7, 1995, and PCT patent publication No. 96/01835, published Jan. 1, 1996; each incorporated herein by reference).

The term "corresponds to" is used herein to mean that a polynucleotide sequence is homologous (i.e., identical) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "5'-TATAC" (SEQ ID NO:23) corresponds to a reference sequence "5'-TATAC" (SEQ ID NO:23) and is complementary to a reference sequence "5'-GTATA" (SEQ ID NO:24).

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length telomerase RNA component gene sequence. Generally, a reference sequence is at least 20 nucleotides in length, frequently at least 25 nucleotides in length, and often at least 50 nucleotides in length. Since two polynucleotides may each comprise (1) a sequence (i.e., a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which for comparative purposes in this manner does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence over a comparison window of at least 20 nucleotide positions, optionally over a window of at least 30–50 nucleotides, wherein the percentage of sequence identity is calculated by comparing the reference sequence to the polynucleotide sequence that may include deletions or additions which total 20 percent or less of the reference sequence over the window of comparison. The reference sequence may be a subset of a larger sequence, for example, as a segment of the full-length telomerase RNA component nucleotide sequence.

Specific hybridization is defined herein as the formation, by hydrogen bonding or nucleotide (or nucleobase) bases, of hybrids between a probe polynucleotide (e.g., a polynucleotide of the invention and a specific target polynucleotide (e.g., a telomerase RNA component or genomic gene sequence), wherein the probe preferentially hybridizes to the specific target such that, for example, a single band corresponding to, e.g., one or more of the RNA species of the telomerase RNA component gene (or specifically cleaved or processed telomerase RNA component species) can be identified on a Northern blot of RNA prepared from a suitable source (e.g., a somatic cell expressing telomerase RNA component). Such hybrids may be completely or only partially base-paired. Polynucleotides of the invention which specifically hybridize to mammalian telomerase RNA component or human telomeric sequences may be prepared on the basis of the sequence data provided herein and available in the patent applications incorporated herein and scientific and patent publications noted above, and according to methods and thermodynamic principles known in the art and described in Sambrooke et al. et al., *Molecular Cloning: A Laboratory Manual*, 2nd Ed., (1989), Cold Spring Harbor, N.Y.; Berger and Kimmel, *Methods in Enzymology, Volume 152, Guide to Molecular Cloning Techniques* (1987), Academic Press, Inc., San Diego, Calif.; Goodspeed et al. (1989) *Gene* 76: 1; Dunn et al. (1989) *J. Biol. Chem.* 264: 13057, and Dunn et al. (1988) *J. Biol. Chem.* 263: 10878, which are each incorporated herein by reference.

As used herein the term "suitable binding conditions" refer to aqueous conditions wherein a mammalian telomerase RNA component associates with its cognate protein component and forms an enzymatically active telomerase holoenzyme capable of catalytic replication, repair, and/or addition of telomeric repeats from a suitable template, generally comprising telomeric repeats; such telomere repeat template may be present or absent. Often, suitable binding conditions can be physiological conditions. "Physiological conditions" as used herein refers to temperature, pH, ionic strength, viscosity, and like biochemical parameters that are compatible with a viable organism, and/or that typically exist intracellularly in a viable cultured mammalian cell, particularly conditions existing in the nucleus of said mammalian cell. For example, the intranuclear or cytoplasmic conditions in a mammalian cell grown under typical laboratory culture conditions are physiological conditions. Suitable in vitro reaction conditions for in vitro transcription cocktails are generally physiological conditions, and may be exemplified by a variety of art-known nuclear extracts. In general, in vitro physiological conditions can comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s), metal chelators, nonionic detergents, membrane fractions, antifoam agents, and/or scintillants.

As used herein, the terms "label" or "labeled" refer to incorporation of a detectable marker, e.g., a radiolabeled amino acid or a recoverable label (e.g. biotinyl moieties that can be recovered by avidin or streptavidin). Recoverable labels can include covalently linked polynucleobase sequences that can be recovered by hybridization to a complementary sequence polynucleotide or PNA; such recoverable sequences typically flank one or both sides of a nucleobase sequence that imparts the desired activity, i.e., inhibition of telomerase activity. Various methods of labeling polypeptides, PNAs, and polynucleotides are known in the art and may be used. Examples of labels include, but are not limited to, the following: radioisotopes (e.g., $^3H$, $^{14}C$, $^{35}S$, $^{125}I$, $^{131}I$), fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). In some embodiments, labels are attached by spacer arms of various lengths, e.g., to reduce potential steric hindrance.

As used herein, the term "statistically significant" means a result (i.e., an assay readout) that generally is at least two standard deviations above or below the mean of at least three separate determinations of a control assay readout and/or that is statistically significant as determined by Student's t-test or other art-accepted measure of statistical significance.

The term "antineoplastic agent" is used herein to refer to agents that have the functional property of inhibiting the development or progression of a neoplasm in a human, and may also refer to the inhibition of metastasis or metastatic potential.

The term "transcriptional modulation" is used herein to refer to the capacity to either enhance transcription or inhibit transcription of a structural sequence linked in cis; such enhancement or inhibition may be contingent on the occurrence of a specific event, such as stimulation with an inducer and/or may only be manifest in certain cell types.

As used herein, the term "transcription regulatory region" refers to a DNA sequence comprising a functional promoter and any associated transcription elements (e.g., enhancer, CCAAT (SEQ ID NO:45) box, TATA (SEQ ID NO:45) box, SP1 site, etc.) that are essential for transcription of a polynucleotide sequence that is operably linked to the transcription regulatory region.

As used herein, the term "receptor-recognition protein" or "rrP" refers to a polypeptide which when bound, either directly or indirectly, to an exogenous polynucleotide or PNA, enhances the intracellular uptake of the exogenous polynucleotide or PNA into at least predetermined one cell type (e.g., hepatocytes). A receptor-recognition protein may include, but is not limited to, the following: a galactose-terminal (asialo-) glycoprotein capable of being internalized into hepatocytes via a hepatocyte asialoglycoprotein receptor, a transferrin polypeptide, and/or other naturally-occurring non-immunoglobulin ligands of cell surface receptors. A receptor-recognition protein may include non-peptide components, such as carbohydrate and/or lipid moieties, in covalent linkage to the polypeptide component (s). In some embodiments, a receptor-recognition protein may comprise multichain proteins and/or multimeric proteins. Various alternative receptor-recognition proteins will be apparent to those of skill in the art and are provided in the published literature.

DESCRIPTION OF PREFERRED EMBODIMENTS

The present invention provides methods, reagents, genetically modified animals and cells, and pharmaceutical compositions relating to the ribonucleoprotein human telomerase. Preferably, the telomerase is of mammalian origin; human telomerase is especially preferred.

The nomenclature used hereafter and the laboratory procedures in cell culture, molecular genetics, and nucleic acid chemistry and hybridization described herein often involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrooke et al. Molecular Cloning: A Laboratory Manual, 2d ed. (1989) Cold Spring Harbor Laboratory Press, Cold Spring Harbor, N.Y., which is incorporated herein by reference).

Oligonucleotides can be synthesized on an Applied BioSystems or other commercially available oligonucleotide synthesizer according to specifications provided by the manufacturer. PNAs and other synthetic nucleotide analogs can be synthesized by any art known method, including use of Applied BioSystems synthesizer equipment provided with approprate reagents, or can be obtained by contract synthesis with a suitable custom manufacturer, such as PerSeptive Biosystems or the like.

Overview

The invention relates to non-nucleotide DNA analogs comprising at least six nucleobases complementary to the hTR repeat region that are highly effective binding to the telomerase RNA component and/or at inhibiting telomerase activity. Specifically, peptide nucleic acids (PNAs) having such complementary sequences are effective and selective inhibitors of telomerase activity and can be formulated and used for a variety of applications, including but not limited to commercial laboratory reagents which inhibit telomerase activity in a telomerase assay, cell sample, cell culture, or whole animal, as well as pharmaceutical uses in veterinary and human subjects, such as for treatment of telomerase-related diseases as described herein.

Human Telomerase RNA Component

The nucleotide sequence of the RNA component of human telomerase is shown below. For convenience, the sequence is shown using the standard abbreviations for ribonucleotides (A is riboadenine, G is riboguanine, C is ribocytidine, and U is uridine). Those of skill in the art recognize that the sequence shown below also shows the sequence of the cDNA, in which the ribonucleotides are replaced by deoxyribonucleotides (with uridine being replaced by thymidine). The sequence is shown in the 5'-3' direction and is numbered for reference. The template sequence region of the RNA component is the sequence defined by nucleotides 46–56 (5'-CUAACCCUAAC-3'; SEQ ID NO:30), which is complementary to a telomeric sequence composed of about one-and-two-thirds telomeric repeat units (the term telomeric repeat sequence typically refers to the sequence: 5'-TTAGGG-3' (SEQ ID NO:1), but optionally can refer to the complementary sequence 5'-GGGTTA-3' (SEQ ID NO:4), and other cyclical sequence permutations of the basic repeat sequence). The portion of the template region complementary to the telomeric repeat sequence is shown in bold and the template region is shown underlined.

human telomerase. Antisense oligonucleotides or analogs comprise a specific sequence of from about 6 to 19 nucleobases, to about 25 to 200 or more (i.e., large enough to form a stable duplex but small enough, depending on the mode of delivery, to administer in vivo, if desired) nucleobases complementary to a specific sequence of nucleotides in the RNA component of human telomerase, preferably in the template region and usually including repeat sequence of human telomerase. The mechanism of action of such molecules can involve binding of the RNA component either to prevent assembly of the functional ribonucleoprotein telomerase, to prevent the RNA component from serving as a template for telomeric DNA synthesis, to destabilize the telomerase RNA component and reduce its half-life, and/or to inhibit transcription of the telomerase RNA component gene, and other effects.

The antisense oligomers of the invention that serve to inhibit telomerase activity in vivo and/or in vitro include the PNA species specifically described herein and other similar analogs. These oligomers can also be used to purify telom-

```
           10         20         30         40         50         60
GGGUUGCGGA GGGUGGGCCU GGGAGGGGUG GUGGCCAUUU UUUGCUAAC CCUAACUGAG 70         80         90        100        110        120
AAGGGCGUAG GCGCCGUGCU UUUGCUCCCC GCGCGCUGUU UUUCUCGCUG ACUUUCAGCG 130        140        150        160        170        180
GGCGGAAAAG CCUCGGCCUG CCGCCUUCCA CCGUUCAUUC UAGAGCAAAC AAAAAAUGUC 190        200        210        220        230        240
AGCUGCUGGC CCGUUCGCCC CUCCCGGGGA CCUGCGGCGG GUCGCCUGCC CAGCCCCCGA 250        260        270        280        290        300
ACCCCGCCUG GAGGCCGCGG UCGGCCCGGG GCUUCUCCGG AGGCACCCAC UGCCACCGCG 310        320        330        340        350        360
AAGAGUUGGG CUCUGUCAGC CGCGGGUCUC UCGGGGCGA GGGCGAGGUU CAGGCCUUUC 370        380        390        400        410        420
AGGCCGCAGG AAGAGGAACG GAGCGAGUCC CCGCGCGCGG CGCGAUUCCC UGAGCUGUGG 430        440        450        460        470        480
GACGUGCACC CAGGACUCGG CUCACACAUG CAGUUCGCUU UCCUGUUGGU GGGGGGAACG

486
CCGAUC
```

For example and not limitation, a human telomerase RNA component polynucleotide can comprise the sequence from nucleotide 1 through 438 of the sequence shown above, however shorter sequences are functional. Typically an hTR sequence comprises nucleotide 45 to nucleotide 209, which is believed sufficient for reconstituting human telomerase holoenzyme in the presence of telomerase protein component: 5'UCUAACCCUAACUGAGAAGGGCGUAG-GCGCCGUGCUUUUGCUCCCCGCGCGC UGUUUUU-CUCGCUGACUUUCAGCGGGCGGAAAAGCCUCGGC CUGCCGCCUUCCAC CGUUCAUUCUAGAGCAAA-CAAAAAAUGUCAGCU GCUGGCCCGUUCGCCCCUCCC-3'(SEQ ID NO:32) or as DNA: 5'TCTAACCCTAACTGAGAAGGGCGTAG-G C G C C G T G C T T T T G C T C C C C G C G C G C TGTTTTTCTCGCT GACTTTCAGCGGGCG-GAAAAGCCTCGGCCTGCCGCCTTCCAC CGTTCAT-TCTAGAGCAAACAAAAAATGTCAGCTGCT GGCCCGTTCGCCCCTCCC-3'. (SEQ ID NO:33) Antisense One especially useful type of nucleic acid of the invention is an antisense (or antigene) oligonucleotide or PNA analog that can be used in vivo or in vitro to inhibit the activity of erase and/or inhibit telomerase activity in human and other mammalian cells.

Additional embodiments directed to modulation of telomerase activity include methods that employ specific antisense PNA polynucleotide analogs complementary to all or part of the human telomerase RNA component (hTR) sequences, such as antisense PNA polymers to the human telomerase RNA component gene or its transcribed RNA, including truncated forms which may be associated with telomerase holoenzyme. Such complementary antisense PNA polymers may include nucleobase substitutions, additions, deletions, or transpositions, so long as specific binding to the relevant target sequence corresponding to telomerase RNA component or its gene is retained as a functional property of the polymer. Complementary antisense PNA polymers include soluble PNA oligomers which can hybridize specifically to telomerase RNA component species and/or prevent transcription of the telomerase RNA component gene (Ching et al. (1989) Proc. Natl. Acad. Sci. U.S.A. 86: 10006; Broder et al. (1990) Ann. Int. Med. 113: 604; Loreau et al. (1990) FEBS Letters 274: 53; Holcenberg et al., W091/11535; W091/09865; W091/04753; W090/13641; and EP 386563, each of which is incorporated herein by reference). Certain antisense polymers of the invention therefore inhibit production of functional telomerase RNA component. Since telomerase RNA component expression (transcription rate and/or RNA stability) is associated with activation and enzymatic activity of telomerase holoenzyme, antisense polymers that prevent transcription of RNA corresponding to telomerase RNA component and/or the interaction of telomerase RNA component with the protein component of human telomerase and/or the interaction of telomerase RNA component to telomeric sequences can inhibit telomerase activity and/or alter a phenotype, such as immortalization or neoplastic transformation, of cells expressing telomerase activity, as compared to a phenotype observed in the absence of antisense polynucleotides. Compositions containing a therapeutically effective dosage of telomerase RNA component antisense PNA polymers can be administered for treatment of diseases which require telomerase activity for cellular pathogenesis (e.g., neoplasia) or to inhibit gamete production or maintenance (i.e., as a contraceptive), if desired. Antisense PNA polymers of various lengths may be produced, although such antisense polymers typically comprise a sequence of about at least 6 consecutive nucleobases which are substantially complementary to a naturally-occurring telomerase RNA component polynucleotide sequence, and typically are perfectly complementary to a human telomerase RNA component template region sequence, often being complementary to the sequence of telomerase RNA component which is complementary to the telomere repeat sequence, or complementary to a portion of the telomerase RNA component which contacts the telomerase polypeptide subunit.

The antisense PNA polymers may comprise soluble species that are administered to the external milieu, either in the culture medium in vitro or in interstitial spaces and bodily fluids (e.g., blood, CSF) for application in vivo. Soluble antisense polymers present in the external milieu can gain access to the cytoplasm and inhibit specific RNA species. In some embodiments the antisense PNA polymers comprise non-PNA moieties, as amino acid moieities, methylphosphonate moieties, C-5 propenyl moieties, 2' fluororibose sugars, or the like (see, Egholm et al. (1992) *J. Am. Chem. Soc.* 114: 1895; Wittung et al. (1994) *Nature* 368: 561; Egholm et al. (1993) *Nature* 365: 566; Hanvey et al. (1992) *Science* 258: 1481, incorporated herein by reference). For general methods relating to antisense polynucleotides, see *Antisense RNA and DNA,* (1988), D. A. Melton, Ed., Cold Spring Harbor Laboratory, Cold Spring Harbor, N.Y.

In addition to the antisense oligomers of the invention, one can construct PNA oligomers that will bind to duplex nucleic acid either in the folded RNA component or in the gene for the RNA component, forming a strand-invasion, strand-displacement D-loop, triple helix-containing or triplex nucleic acid to inhibit telomerase activity and/or transcription or processing of the hTR gene. Such oligomers of the invention are constructed using the base-pairing rules of triple helix formation and the nucleotide sequence of the RNA component (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci.* (U.S.A.) 83: 9591, incorporated herein by reference). Such non-nucleotide oligomers can block telomerase activity in a number of ways, including by preventing transcription of the telomerase gene or by binding to a duplex region of the RNA component of telomerase in a manner that prevents the RNA component either from forming a functional ribonucleoprotein telomerase or from serving as a template for telomeric DNA synthesis. Typically, and depending on mode of action, the oligomers of the invention comprise a specific sequence of from about 6 to about 25 to 200 or more (i.e., large enough to form a stable triple helix but small enough, depending on the mode of delivery, to administer in vivo, if desired) nucleotides complementary (in this context, complementary means able to form a stable triple helix or to strand-invade or displace or form D-loop structures) to a specific sequence in the RNA component of telomerase or the gene for the RNA component of telomerase. In certain variations, complementary or corresponding sequence PNAs can be targeted near the promoter region of the hTR gene, preferably about 100–1000 nucleotides upstream of the hTR promoter, to induce D-loop formation and induce transcription of hTR in cells in which hTR expression is substantially quiescent (e.g., hTR expression is undetectable or subnormal for the cell type).

In addition to the antisense PNA oligomers of the invention, sense oligomers identical in sequence to at least a portion of the RNA component of human telomerase can also be used to inhibit or induce telomerase activity. Oligomers of the invention of this type are characterized in comprising either (1) less than the complete sequence of the RNA component needed to form a functional telomerase enzyme or (2) the complete sequence of the RNA component needed to form a functional telomerase enzyme as well as a substitution or insertion of one or more nucleobases that render the resulting RNA non-functional. The mechanism of action of such non-nucleotide oligomers thus involves the assembly of a non-functional ribonucleoprotein telomerase or the prevention of assembly of a functional ribonucleoprotein telomerase, such as by competitive inhibition of binding of hTR RNA to telomerase apoenzyme protein. Sense oligomers of the invention of this type typically comprise a specific sequence of from about 5, 10, 20, 50, 100, 200, 400, or more nucleobases identical to a specific sequence of nucleotides in the RNA component of mammalian, preferably human, telomerase.

In addition, antisense polynucleotides can comprise a derivatized substituent which is substantially non-interfering with respect to hybridization to the RNA component of a mammalian telomerase. Antisense polymers that have been modified with appended chemical substituents may be introduced into a metabolically active eukaryotic cell to hybridize with a telomerase RNA component of telomerase in the cell. Typically such antisense polymers are derivatized, and additional chemical substituents are attached, either during or after polymer synthesis, respectively, and are thus localized to a complementary sequence in the telomerase RNA component where they produce an alteration or chemical modification to a local RNA sequence and/or to the telomerase protein component. Examples of peptide sequences which can be linked to a PNA of the invention, such as for facilitating uptake of PNA into cells, include, but are not limited to: an 11 amino acid peptide of the tat protein of HIV and/or a 20 residue peptide sequence which corresponds to amino acids 84–103 of the p16 protein (see, Fahraeus et al. (1996) *Current Biology* 6: 84, incorporated herein by reference) and/or a suitable portion of a 60-amino acid long homeodomain of Antennapedia (Derossi et al. (1994) *J. Biol. Chem.* 269: 10444, incorporated herein by reference).

Polynucleotides can be linked to a telomerase-modulating PNA of the invention, typically at the amino-terminus or carboxy-terminus. Such polynucleotides can enhance cellular uptake. In one variation, the charged backbone of the linked polynucleotide enhances binding to cationic lipids, and facilitates formation and/or stability or other desired property(ies) of PNA:lipid delivery complexes. PNA:lipid delivery complexes include but are not limited to: liposomes comprising PNA, immunoliposomes comprising PNA, cationic lipid:PNA aggregates, polylysine:lipid:PNA complexes, polyarginine:lipid:PNA complexes, receptor recognition protein (rrP):lipid:PNA complexes, receptor recognition protein (rrP):polylysine:lipid:PNA complexes, receptor recognition protein (rrP):polyarginine:lipid:PNA complexes and the like.

Preferred attached chemical substituents include: europium (III) texaphyrin, cross-linking agents, psoralen, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are particularly preferred chemical substituents where local cleavage of a polynucleotide sequence is desired (Hertzberg et al. (1982) *J. Am. Chem. Soc.* 104: 313; Hertzberg and Dervan (1984) *Biochemistry* 23: 3934; Taylor et al. (1984) *Tetrahedron* 40: 457; Dervan, PB (1986) *Science* 232: 464). Preferred attachment chemistries include: direct linkage, e.g., via an appended reactive cyteine group (Corey and Schultz (1988) *Science* 238: 1401, which is incorporated herein by reference) and other direct linkage chemistries, although streptavidin/biotin and digoxigenin/anti-digoxigenin antibody linkage methods may also be used. Methods for linking chemical substitutents are provided in U.S. Pat. Nos. 5,135,720, 5,093,245, and 5,055,556, which are incorporated herein by reference. Other linkage chemistries may be used at the discretion of the practitioner. Non-nucleotide PNA polymers which correspond to all or a substantial portion of a mammalian telomerase RNA component (i.e., "sense" polymers) may also be derivatized and used to react with telomerase proteins and or the telomerase component gene or telomeric repeat sequences in the genome and produce adducts or other modification of the chemical environment at such regions of the genome.

In an aspect of the invention, the telomerase-modulating PNA is introduced into a mammalian cell by a transfection method. In an embodiment, the transfection methods comprise: (1) forming a transfection complex consisting essentially of a PNA, and a lipid component consisting essentially of a neutral and/or cationic lipid, optionally including a quaternary ammonium detergent and/or a lipopolyamine, optionally including a polycation (poly lysine, polyarginine, and the like), optionally including a receptor-recognition molecule that binds to a predetermined cell surface receptor (e.g., asialoglycoprotein receptor), and (2) contacting cells with the transfection complex, which can be in vitro, ex vivo, or in vivo. In embodiments where a receptor recognition protein is included in the transfection complex, cells expressing the predetermined cell surface receptor with a composition comprising the receptor-recognition transfection complex under physiological transfection conditions which permit uptake of the PNA into said cells.

Therapeutic and Prophylactic Aspects

Because telomerase is active only in tumor, germline, and certain stem cells, for example stem cells of the hematopoietic system, other normal cells are not affected by telomerase inhibition therapy using non-nucleotide PNA polymers of the present invention. Steps can also be taken to avoid contact of the telomerase inhibitor with germline or stem cells, although this may not be essential. For instance, because germline cells express telomerase activity, inhibition of telomerase may negatively impact spermatogenesis and sperm viability, and telomerase inhibitors may be effective contraceptives or sterilization agents. This contraceptive effect may not be desired, however, by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient, or more localized administration can be used.

These methods can be carried out by delivering to a patient, more particularly to diseased cells, a functional non-nucleotide PNA polymer of the invention to the cell. For instance, the non-nucleotide PNA polymer can be delivered in a liposome or other delivery enhancement formulation. In certain embodiments, the PNA comprises a moiety which enhances uptake into cells or subcellular compartments (e.g., nucleus); such moieties can include polypeptide sequences such as an 11 animo acid peptide of the tat protein of HIV and/or a 20 residue peptide sequence which corresponds to amino acids 84–103 of the p16 protein (see, Fahraeus et al. (1996) *Current Biology* 6: 84, incorporated herein by reference) and/or a suitable portion of a 60-amino acid long homeodomain of Antennapedia (Derossi et al. (1994) *J. Biol. Chem.* 269: 10444, incorporated herein by reference).

Sense and antisense PNAs that hybridize near the hTR promoter, typically within 100–1000 nucleotides, can be used to activate or inhibit telomerase activity in various human cells that otherwise lack detectable telomerase activity due to low levels of expression of the RNA component or a protein component of telomerase. If the telomerase RNA component is not sufficient to stimulate telomerase activity, then the PNA can be introduced along with genes expressing the protein components of telomerase to stimulate telomerase activity. Thus, the invention provides methods for treating a condition associated with the telomerase activity within a cell or group of cells by contacting the cell(s) with a therapeutically effective amount of a PNA that alters telomerase activity in that cell.

Cells that incorporate PNAs having the property of stimulating hTR gene expression by D-loop formation near the promoter of the telomerase RNA gene can exhibit an increase in telomerase activity and an associated extended replicative life span. Such therapy can be carried out ex vivo on cells for subsequent introduction into a host or can be carried out in vivo. The advantages of stabilizing or increasing telomere length by adding PNA ex vivo to normal diploid cells include: telomere stabilization can arrest cellular senescence and allow potentially unlimited proliferative capacity of the cells; and normal diploid cells with an extended life span can be cultured in vitro for drug testing, virus manufacture, transplantation, or other useful purposes. In particular, ex vivo amplified stem cells of various types can be used in cell therapy for particular diseases, as noted above. Telomere stabilization can also suppress cancer incidence in replicating cells by preventing telomeres from becoming critically short as cells near crisis.

Cells that can be treated with PNA species that activate hTR transcription by D-loop formation at the promoter include but are not limited to hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

Typically, the therapeutic methods of the invention involve the administration of a non-nucleotide oligomer that functions to inhibit or stimulate telomerase activity under in vivo physiological conditions and is sufficiently stable under those conditions. As noted above, modified nucleic acids may be useful in imparting such stability, as well as for ensuring delivery of the PNA oligomer to the desired tissue, organ, or cell. Methods useful for delivery of oligonucleotides for therapeutic purposes are described in Inouye et al., U.S. Pat. No. 5,272,065, incorporated herein by reference.

In related aspects, the invention features pharmaceutical compositions including a therapeutically effective amount of a telomerase inhibitor PNA or telomerase activator PNA of the invention. Pharmaceutical compositions of telomerase inhibitors of the invention include a PNA species which comprises at least six contiguous nucleobases complementary to a hTR template region sequence, or combinations of such species and/or with other pharmaceuticals in a pharmaceutically acceptable carrier or salt. Other pharmaceutical compositions of the invention comprise a telomerase activator PNA preparation.

The therapeutic agent can be provided in a formulation suitable for parenteral, nasal, oral, or other mode of administration. See PCT patent publication No. 93/23572, supra.

In another aspect of the invention, buffered aqueous solutions comprising at least one telomerase-inhibitory or activating PNA species of the invention at a concentration of at least 1 nM but not more than about 100 mM is formulated for administration, usually at a concentration of about 0.1 to 10 mM, typically by intravenous route, to a patient undergoing antineoplastic or antihelminthic chemotherapy. The buffered aqueous solutions of the invention may also be used, typically in conjunction with other established methods, for organ culture, cell culture, delivery to transformed cells, and ex vivo cellular therapies. Nonaqueous formulations, such as lipid-based formulations are also provided, including stabilized emulsions. The telomerase-modulating PNA compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

Isolation of Telomerase Protein Component

The PNA reagents of the present invention also allow the isolation of the telomerase holoenzyme protein components of human as well as other mammalian telomerase enzymes. Thus, the invention provides methods for isolating and purifying the protein components of human telomerase, as well as for identifying and isolating nucleic acids encoding the protein components of human telomerase.

Several different methods can be employed to achieve identification and isolation of the protein components. For instance, one can use affinity capture of the enzyme or partially denatured enzyme using as an affinity ligand either (1) PNA having nucleobase sequences complementary to the telomerase RNA component to bind to the RNA component of the intact enzyme; or (2) the PNA mimetics of the RNA component to bind the protein components of a partially or fully denatured enzyme. The ligand can be affixed to a solid support or chemically modified (e.g., biotinylated) for subsequent immobilization on the support. Exposure of cell extracts containing human telomerase, followed by washing and elution of the telomerase enzyme bound to the support, provides a highly purified preparation of the telomerase enzyme. The protein components can then be optionally purified further or directly analyzed by protein sequencing. The protein sequence determined can be used to prepare primers and probes for cloning the cDNA or identifying a clone in a genomic bank comprising nucleic acids that encode a protein component of telomerase.

Figure 2A:
FIG. 2. Schematic description of purification of telomerase by use of capture PNA and release PNA species. (Panel A) Branch migration between two polynucleotides in solution equilibrium. (Panel B) Displacement of a strand of a double-stranded helix by strand invasion and total displacement by a release PNA forming a stable hybrid having greater thermodynamic stability. (Panel C) Scheme for capture and release of telomerase using PNA capture and release species and exemplified with a streptavidin-coated bead (B: biotin group; S: streptavidin linked to bead).
Figure 2B:
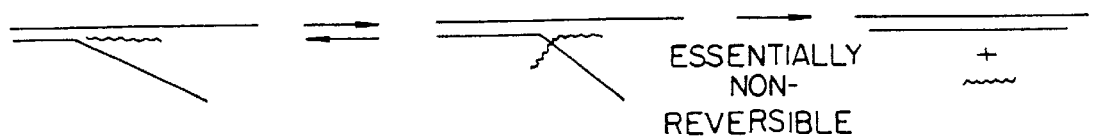
Figure 2C:
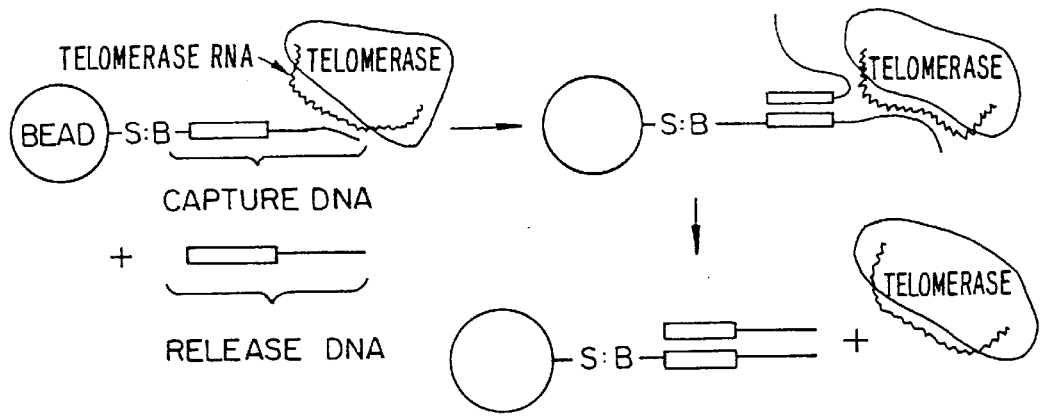

Affinity capture of telomerase utilizing an engineered capture PNA having nucleobase sequences complementary to at least 10 nucleotides of the RNA component and adjacent nucleobase sequence of at least 10 nucleobases, preferably 13 or more nucleobases, which is not present in the RNA component. Preferably, the portion of the PNA complementary to the hTR complements a portion of the hTR which is non-essential for association of the hTR to the telomerase protein components, so that binding of the PNA to the hTR will not disrupt association of the hTR with the telomerase protein component. The capture PNA is engineered to contain a release tag, wherein the release tag is a sequence of nucleobases not present in the hTR nucleotide sequence. The capture PNA is immobilized or comprises a label (e.g., biotinyl moieties, hybridizable sequence) that can be bound by an immobilized ligand. The capture PNA is contacted with a solution containing mammalian telomerase, preferably human telomerase, and other undesired constituents of the solution or extract. The capture PNA binds to the telomerase RNA component and forms a PNA:telomerase complex, which is immobilized or otherwise captured in a manner suitable for substantial isolation of the PNA:telomerase complexes from the undesired components of the solution or extract. Following separation of the immobilized PNA:telomerase complexes from the undesired constituents, the telomerase holoenzyme can be released by contacting the complexes with a release PNA. A release PNA comprises a nucleobase sequence complementary to the release tag of the capture PNA, wherein the release tag is a sequence of nucleobases not present in the hTR nucleotide sequence, and an adjacent nucleobase sequence which is complementary to the portion of the capture PNA complementary to the RNA component. The release PNA effects release of the hTR (and telomerase holoenzyme) from the capture PNA by strand displacement, or "zippering", as shown in FIG. 2, panel C. Since the rank of relative thermodynamic stability is: PNA:PNA>PNA:RNA>RNARNA>RNA:DNA>DNADNA, PNAs can be used to reversibly capture RNA and DNA species in a sequence-specific manner and then release them when desired using a release PNA to displace the RNA or DNA from the capture PNA. Affinity capture using the immobilized capture PNA followed by release with the strand-invading release PNA can then be used to isolate the enzyme. The general method can be used to isolate essentially any desired RNA or DNA species having a predetermined sequence.

Telomerase RNA binding or telomerase activity assays for detection of specific binding proteins and activity can be used to facilitate the purification of the telomerase enzyme and the identification of nucleic acids that encode the protein components of the enzyme. For example, PNAs comprising RNA component sequences can be used as affinity reagents to isolate, identify, and purify peptides, proteins or other compounds that bind specifically to a sequence contained within the RNA component, such as the protein components of human telomerase. Several different formats are available, including gel shift, filter binding, footprinting, Northwestern (RNA probe of protein blot), and photocrosslinking, to detect such binding and isolate the molecules that bind specifically to the RNA component. These assays can be used to identify binding proteins, to track purification of binding proteins, to characterize the RNA binding sites, to determine the molecular size of binding proteins, to label proteins for preparative isolation, and for subsequent immunization of animals for antibody generation to obtain antibodies for use in isolating the protein or identifying a nucleic acid encoding the protein in a coupled transcription/translation system.

Purification of Mammalian Telomerase Protein Component

Mammalian telomerase protein component can be purified by the method disclosed in U.S. patent application Ser. No. 08/288,501, filed Aug. 10, 1994, which is incorporated herein by reference, from telomerase-expressing cells, such as HT1080 cells, 293 cells, and other suitable immortalized cell lines. For example and not limitation, human telomerase can be purified from cell extracts. Mammalian telomerase extracts can be stripped of the telomerase RNA component, if desired, by treatment with an RNAse activity or other suitable means to dissociate and/or degrade the telomerase RNA component while leaving telomerase protein component substantially intact and capable of reconstitution with addition of exogenous telomerase RNA component, or a PNA mimetic thereof such as may be produced recombinantly or the like. The telomerase protein component thus purified, and optionally stripped of endogenous telomerase RNA component, can be used in the agent screening assays described herein, and for other uses.

Preferably, for determining binding of telomerase RNA component or a PNA mimetic to immobilized telomerase protein component, the telomerase RNA component species is labeled with a detectable marker, typically a biotinyl group, a fluorescent moiety, or a radiolabeled incorporated nucleotide or PNA nucleobase. Suitable labeling for telomerase protein component includes, but is not limited to, radiolabeling by incorporation of a radiolabeled amino acid (e.g., $^{14}$C-labeled leucine, $^{3}$H-labeled glycine, $^{35}$S-labeled methionine), radiolabeling by post-translational radioiodination with $^{125}$I or $^{131}$I(e.g., Bolton-Hunter reaction and chloramine T), labeling by post-translational phosphorylation with $^{32}$p (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the species is immobilized by linkage to a substrate, the other component is generally labeled with a detectable marker.

In embodiments where a telomerase RNA component or telomerase protein component is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci.* (U.S.A.) 83: 5889). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one embodiment, candidate therapeutic PNAs are identified by their ability to block the binding of a telomerase protein component to a telomerase RNA component and/or to inhibit telomerase activity in a suitable activity assay (e.g., TRAP assay; see, WO 95/13381 published May 18, 1995). Typically, a telomerase RNA component used in these methods comprises a naturally occurring mammalian telomerase RNA component sequence (e.g., a human RNA component), although mutant telomerase RNA component sequences are sometimes used if the mutant telomerase RNA component binds to the telomerase protein component under control assay conditions (e.g., physiological conditions).

PNA species which specifically inhibit human telomerase activity are candidate antineoplastic agents, which are formulated for administration to a patient having a neoplasm. Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

Assays for detecting the ability of PNA species to inhibit or augment the telomerase protein component:telomerase RNA component binding and/or enzymatic activity of telomerase provide for facile high-throughput screening of banks of PNA species having varying nucleobase sequences and terminal modifications and/or terminal appended amino or imino acid residues, wherein the screens identify telomerase antagonist PNA species or agonist PNA species. Such antagonists and agonists may modulate telomerase activity and thereby modulate telomere repair competence and replicative potential.

Administration of an efficacious dose of an PNA capable of specifically inhibiting telomerase activity to a patient can be used as a therapeutic or prophylactic method for treating pathological conditions (e.g., cancer, inflammation, lymphoproliferative diseases, autoimmune disease, neurodegenerative diseases, and the like), which are effectively treated by modulating telomerase activity and DNA repair and replication.

The telomerase-modulating PNA species of the present invention can be administered as a pharmaceutical composition comprising the compound in combination with a pharmaceutically acceptable excipient. Such excipients include water, saline, Ringer's solution, dextrose solution, and solutions of ethanol, glucose, sucrose, dextran, mannose, mannitol, sorbitol, polyethylene glycol, phosphate, acetate, gelatin, collagen, and the like. One may additionally include other suitable preservatives, stabilizers and antimicrobials, antioxidants, buffering agents and the like. A thorough discussion of pharmaceutically acceptable excipients is available in *Remington's Pharmaceutical Sciences,* 2nd Ed., Mack Publishing Co. Typically, a PNA of the invention is formed in a pharmaceutical dosage form comprising an excipient and not less than 1 µg nor more than about 100 grams of at least one telomerase-modulating PNA species of the invention. In another aspect of the invention, buffered aqueous solutions comprising at least one telomerase-modulating PNA species of the invention at a concentration of at least 1 nM but generally not more than about 100 mM is formulated for administration, usually at a concentration of about 0.1 µM to 10 mM, typically by intravenous route or via in infusion pump for localized delivery (e.g., to a solid tumor) or sustained dosing.

Alternatively, one may incorporate or encapsulate the telomerase-modulating PNAs in a suitable polymer matrix, liposome or membrane, thus providing a sustained release delivery device suitable for implantation near the site to be treated locally. In general, with sustained release delivery, the formulations are constructed so as to achieve a constant concentration which will be bioequivalent to about 100 times the serum level of PNA of 10 times the tissue concentration. Nonaqueous formulations, such as lipid-based formulations are also provided, including stabilized emulsions. The telomerase-modulating PNA compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

The amount of telomerase-modulating PNA required to treat any particular neural disorder will of course vary depending on the nature and severity of the disorder, the age and condition of the patient, and other factors readily determined by one of skill in the art. Suitable dosages are from 1 ng/kg to about 1000 mg/kg, more preferably 1 µg/kg to about 100 mg/kg.

As will be apparent to those of skill in the art upon reading of this disclosure, the present invention provides valuable reagents relating to human telomerase, as well as a variety of useful therapeutic and diagnostic methods. The above description of necessity provides a limited sample of such methods, which should not be construed as limiting the scope of the invention. Other features and advantages of the invention will be apparent from the following examples and claims.

The following examples describe specific aspects of the invention to illustrate the invention and provide a description of the methods used to isolate and identify the RNA component of human telomerase for those of skill in the art. The examples should not be construed as limiting the invention, as the examples merely provide specific methodology useful in understanding and practice of the invention.

EXPERIMENTAL EXAMPLES

The abbreviations used are: RNA-P, RNA polymerase; PS, phosphorothioate; PNA, peptide nucleic acid; hTR, the RNA component of human telomerase; TRAP; Telomeric repeat amplification protocol; TS primer, oligonucleotide primer that can be extended by telomerase; $IC_{50}$, Concentration of inhibitor required to eliminate 50% of enzymatic activity; ITAS, internal amplification standard; AEBSF, 4-(2-aminoethyl)benzenesulfonyl fluoride; PCR, polymerase chain reaction.

Overview

Telomeres are genetic elements located at the ends of all eukaryotic chromosomes and preserve genome stability and cell viability by preventing aberrant recombination and degradation of DNA. The human telomeric DNA sequence is $(TTAGGG)_n$. The length of these repeat tracts varies from 15–20 kB in germ line cells to 5–12 kB in peripheral blood leukocytes. Telomeric repeats decrease during aging of human somatic cells in vitro and in vivo due to the end replication problem, which, in germ cells, is compensated for by the activity of telomerase. Telomerase is an RNA-dependent DNA polymerase that synthesizes telomeric repeats at the 3' end of the leading DNA strand. The RNA component of human telomerase (hTR) contains an 11 base sequence complementary to the telomere repeat and functions as a template for extension of chromosome ends. Telomerase activity is detected in 85–95% of human tumors, and is logically required for sustained tumor proliferation. Maintenance of telomere length in tumor cell lines can be prevented by the expression of antisense RNA complementary to the hTR, leading to cell crisis (Feng et al. (1995) Science 269: 1236), and telomerase inhibition is believed to suppress tumor growth.

Figure 1B:
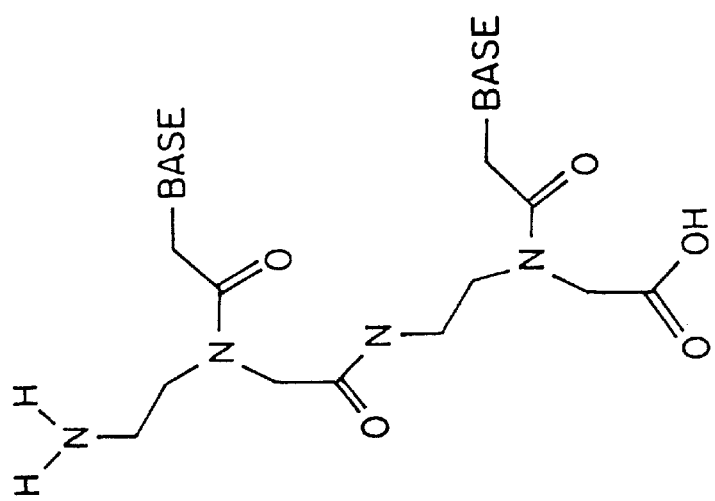
Figure 1A:
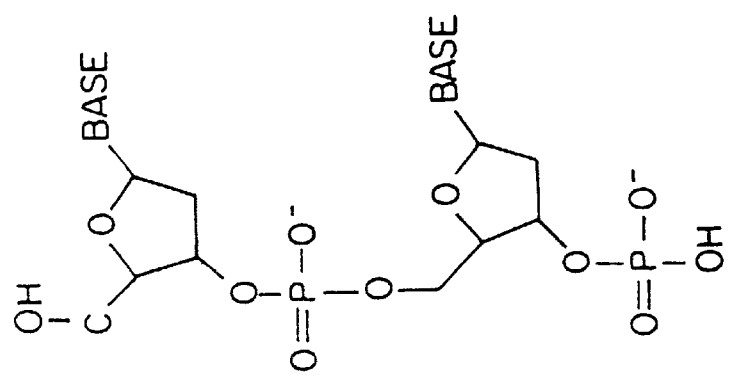

DNA oligonucleotides can inhibit telomerase, but this inhibition requires that oligonucleotides be relatively long (18–40 nucleotides) and be present at high concentrations (Collins et al. (1995) Cell 81: 677; Shippen-Lentz and Blackburn (1990) Science 247: 546). Chemically modified oligonucleotides or non-nucleotide polymers that hybridize with enhanced affinity to telomerase were tested for the ability to act as more effective inhibitors of telomerase activity. One class of modified oligonucleotides, peptide nucleic acids (PNAs), contains a nonionic backbone in which the deoxyribose linkages have been replaced by N-(2-aminoethyl) glycine units that are linked to the nucleotide bases via the glycine amino nitrogen through a methylenecarbonyl linker (FIG. 1). The uncharged nature of the PNA internucleotide linkage increases the melting temperature of associating strands, increases in the rate of association with targeted nucleic acids, and affords greater resistance to degradation by proteases or nucleases.

PNAs are polyamide oligomers that hybridize to complementary sequences with high affinity and enhanced rates of association. These properties endow PNAs with unique potential as functional probes and effective inhibitors of basic biological processes.

In an effort to develop highly efficient telomerase inhibitors that combine chemical stability with efficient and selective inhibition we examined the inhibition of human telomerase by modified oligonucleotide motifs that are known to be nuclease-resistant. To this end, we assayed inhibition of telomerase activity by PNA and PS oligonucleotides.

Summary

PNAs were shown to recognize the RNA component of human telomerase (hTR) and inhibit activity of the enzyme within cell extracts or whole cells in picomolar to nanomolar concentrations. Inhibition of telomerase activity by PNAs is specific and potent and depends on targeting of exact functional boundaries of hTR template region. Inhibition by PNAs is 10–50 fold more efficient than the analogous phosphorothioate (PS) oligomers. In contrast to high selectivity of inhibition by PNAs, PS oligomers also inhibit telomerase in a nonsequence-selective fashion. These results demonstrate that the specificity and high affinity of PNA recognition can be employed to control the enzymatic activity of ribonucleoproteins, and that PNAs possess important advantages relative to PS oligomers in both the affinity and the specificity of their recognition. These observations provide effective inhibitors of telomerase activity and affinity probes of telomerase structure.

The results of the demonstrations hereinbelow show that PNAs can inhibit telomerase efficiently and at low concentrations. PNAs inhibit telomerase activity when present at lower concentrations than analogous (sequence identical) phosphorothioate (PS). PS oligomers nonselectively inhibit telomerase. These results show that PNAs possess distinct advantages relative to PS oligomers and can be developed as inhibitors of ribonucleoproteins.

MATERIALS AND METHODS

Preparation of PNA and PS Oligomers—PNA monomers were obtained from PerSeptive Biosystems. Anhydrous dimethyl formamide was purchased from Aldrich. Peptide monomers and derivatized resin were obtained from Peptides International. PNAs were synthesized manually following t-boc peptide chemistry as described (Norton et al. (1995) *Bioorganic and Medicinal Chemistry* 3: 437, incorporated herein by reference) with the following modifications. The syntheses for PNAs I–VIII, IX and X, and XI–XIII were accomplished simultaneously. These PNAs possess the same sequence at their carboxy termini. Synthesis was carried out from carboxy to amino terminus and, as a desired PNA length was reached, a fraction of total resin was removed. The removed resin was capped with glycine to complete the desired polymer chain. Following complete synthesis the product was cleaved off the resin and deprotected by treatment with trifluormethanesulfonic acid:trifluoroacetic acid: m-cresol:thioanisole (2:6:1:1) for 1 hour. The product was precipitated with diethylether and collected. Following purification by reverse phase HPLC as described (Norton et al. (1995) op.cit) the identity of each PNA was confirmed by mass spectroscopy. PS oligonucleotides were synthesized using reagents obtained from Applied Biosystems. PS and phosphodiester oligonucleotides were synthesized using an Applied Biosystems 451 DNA synthesizer.

Preparation of cell extracts and of permeabilized cells—Cells were derived from a human immortal primary breast epithelial cell line (HME50-5) that expresses telomerase at high levels. Cell extracts were obtained by resuspending a 100,000 cell pellet into 200 $\mu$L of lysis buffer (0.5% 3-[3-cholamidopropyl-dimethylammonio]-1-propane-sulfonate (CHAPS), 10 mM Tris-HC1, pH 7.5, 1 mM ethylenebis(oxyethylene-nitrilo)tetraacetic acid (EGTA), 5 mM $\beta$-mercaptoethanol, 0.1 mM 4-(2-aminoethyl)benzenesulfonyl fluoride (AEBSF), 10% glycerol). The suspension was mixed by pipetting at least three times and kept on ice for 30 minutes. The lysate was centrifuged at 16,000×g for 20 minutes at 4° C., and 160 $\mu$L of the supernatant was collected. The cells were then diluted 10-fold to obtain a 50 cell equivalent/$\mu$L stock suspension, aliquoted, frozen in liquid nitrogen, and stored at −80° C. These aliquots were utilized throughout our experiments to ensure consistency.

To examine the ability of PNAs to inhibit telomerase activity within permeabilized cells HME50-5 cells were treated with a buffered solution containing a relatively low concentration of detergent (20 mM Tris-HCl, pH 8.3, 1.5 mM $MgCl_2$, 68 mM KCl, 0.5% Tween 20, 1 mM EGTA, 5.0% glycerol, and 0.1 mM AEBSF). The telomerase activity in these cells was not further purified, and permeablized cells were incubated with PNA and PS oligomers prior to assay for telomerase activity.

A further control experiment was performed to ensure that the observed inhibition was due to PNA entry into permeablized cells The TRAP assay was utilized to compare the level of telomerase activity retained inside permeabilized cells to activity which leaks into solution. This control was necessary to ensure that the observed inhibition was due to PNA inhibition of telomerase within cells. Permeabilized cells were centrifuged and the cell pellet and the cell-free supernatant were separately examined for telomere activity using the TRAP assay. Greater than 80% of telomerase activity remained associated with the cell pellet after this mild treatment, confirming that telomerase is largely retained inside permeablized cells.

Measurement of Telomerase Activity—Telomerase activity was determined using the telomere repeat amplification protocol (TRAP) assay essentially as described (Piatyszek et al. (1995) *Methods in Cell Science* 17: 1, incorporated herein by reference) with the modification that the cellular extract was preincubated at 25° C. for 30 minutes with the PNA at the concentrations indicated. Following preincubation 3 $\mu$l of the cellular extract plus PNA was added to a PCR tube containing 46 $\mu$l of reaction buffer (20 mM Tris-HCl, pH 8.3, 1.5 MM $Mgcl_2$, 68 MM KCl, 0.05% Tween-20, 1 mM EGTA), 50 $\mu$M dNTPs, 0.1 $\mu$g TS primer (5'AATCCGTCGAGCAGAGTT-3'; SEQ ID NO:34), 5 attg ITAS template (25), 0.5 $\mu$M T4 gene 32 protein, 2 Units Taq polymerase, 4 $\mu Ci^{32}P$-$\alpha$ dCTP) above a wax barrier separating 0.1 $\mu$g of the CX, reverse primer (5'-CCCTTACCCTTACCCTTACCCTAA-3'; SEQ ID NO:34), and incubated for 30 minutes to allow telomerase to elongate the TS primer. The tubes were transferred to a PCR thermocycler set at 94° C. for 3 minutes to melt the wax barrier, cycled 30 times (30 seconds at 95° C., 30 seconds at 55° C. and 30 seconds at 72° C.) followed by a 3 minute extension at 72° C. The samples were frozen at −80° C. and the wax barrier removed. The solution containing the PCR products (40 $\mu$L) was added to 3.3 $\mu$L of loading buffer and 20 $\mu$l was loaded onto a 10% non-denaturing polyacrylamide gel and separated by electrophoresis at 180 volts for 45 minutes followed by 280 volts for 1 hour and 45 minutes. Gels were fixed for 30 minutes (1:1 ethanol: water, 0.5M NaCl, 40 mM NaOAc, pH 4.2) then exposed to a phosphorimager screen for quantitation. Phosphorimager analysis was performed utilizing a Molecular Dynamics model 425F phosphorimager. Data was processed using ImageQuant software version 3.3.

Estimation of $IC_{50}$ values or the Inhibition of Telomerase Activity—Varied concentrations of PNA were added to cell extracts containing the TS primer. Telomerase products were visualized by gel electrophoresis and the extent of inhibition was quantified by phosphorimager analysis by evaluating each lane of the gels separately. The lanes were further separated into two areas for evaluation; one for the internal amplification standard (ITAS) and the other for all telomerase products. A ratio of telomerase products to ITAS was determined and compared to a positive control in which no PNA had been added. This ratio was taken to indicate telomerase activity with the ratio of the positive control being assigned 100% activity. The extent of inhibition as a function of the concentration of the added PNA was plotted and these graphs were utilized to derive the $IC_{50}$.

Measurement of $K_{m\ app}$ for TS primer—Telomerase assays were performed essentially as described above with slight modifications. Both the TS and CX primers (0.1 $\mu$g) were placed below the wax barrier and the concentration of TS primer was varied from 0 to 60 nM, above the wax barrier, in the reaction mixture. The reaction was allowed to proceed for 30 minutes at 25° C. followed by PCR as described. The products were quantitated as described with telomerase activity relative to control plotted versus the TS primer concentration. The TS primer concentration at which 50% of maximal telomerase activity was achieved was taken to be a $K_m$ app of telomerase for the TS primer.

RESULTS

TRAP assay as a Measure of Telomerase Activity—Telomerase activity was measured using the telomeric repeat amplification protocol (TRAP). Rather than measure the change in chromosome length over time, a process that requires weeks to produce definitive results and measures telomerase activity only indirectly, the TRAP assay measures the elongation of a short oligonucleotide primer (TS primer) known to act as an efficient substrate of telomerase.

Cell extracts from a human immortal breast epithelial cell line, HME50-5, expressing telomerase were preincubated with PNAs to allow recognition of complementary sequences by Watson-Crick base-pairing. The TS primer was then added to initiate chain elongation by telomerase. Following elongation of the TS primer, the mixture was transferred to a thermocycler and polymerase chain reaction (PCR) was performed to amplify the products. Two potential template DNAs were present, and amplification products were primed from either an internal amplification standard (ITAS) or from the product of telomerase elongation of the TS primer. These amplification products were separated by gel electrophoresis and quantitated separately. A ratio of the amount of amplified products of telomerase activity to that derived from amplification of the ITAS standard was determined and compared to a positive control to which no PNA was added. This comparison allowed calculation of the inhibition of telomerase activity due to a given concentration of PNA.

Figure 3A:
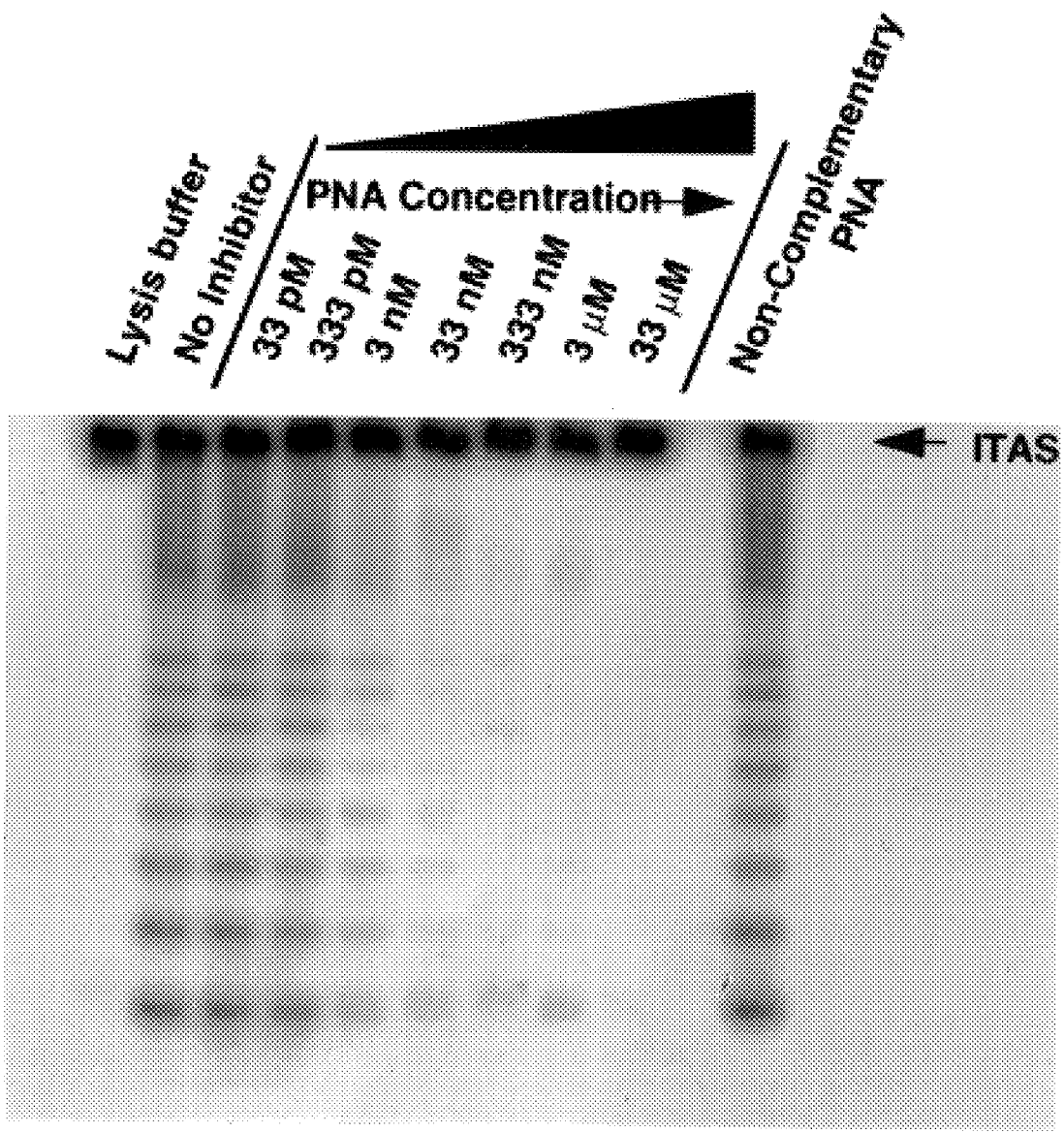
FIG. 3. (Panel A) TRAP assay results (products of reaction after gel electrophoresis) showing inhibition of telomerase activity by PNA XII; the location of the internal amplification standard (ITAS) is noted. (Panel B) Results of inhibition of telomerase activity in TRAP assay of Panel A graphed as a function of the concentration of PNA XII.
Figure 3B:
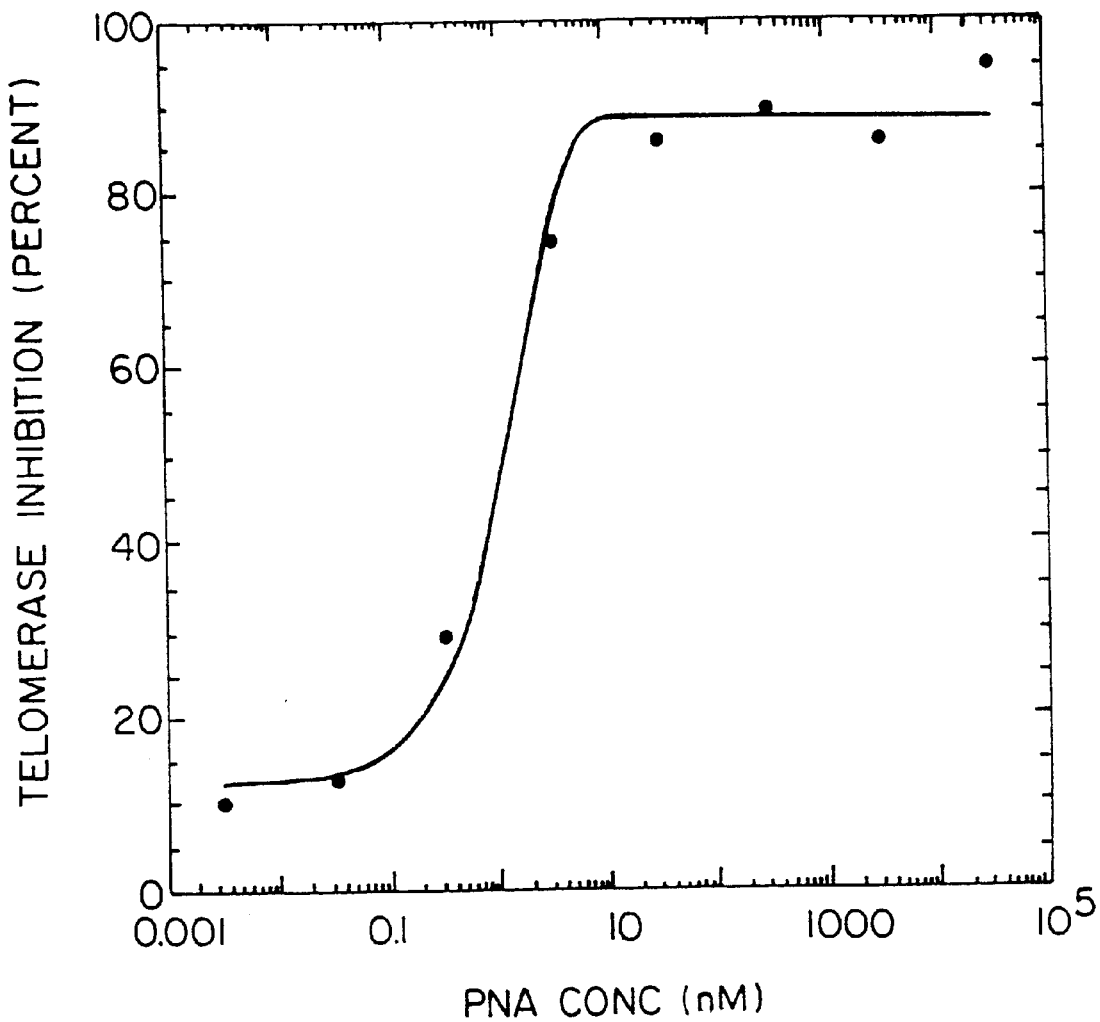

Inhibition of Telomerase Activity in Purified Extracts by PNAs—PNA oligomers of varied lengths were evaluated for their ability to inhibit telomerase activity (Table 1). PNAs were incubated with the crude extracts containing telomerase for thirty minutes to allow recognition of telomerase, after which the TS primer was added to initiate elongation. PNAs I, II, III, and IV were targeted to the 11 base template sequence and were shown to inhibit telomerase (Table I). Inhibition increased with the length of PNA, as the 6, 9, 10, and 11 base PNAs possessed $IC_{50}$ values of 30, 1, 0.2, and 0.01 µM respectively. Addition of PNAs did not inhibit amplification of the control ITAS template, demonstrating that PNAs do not inhibit Taq polymerase or prevent hybridization of the amplification primers. Longer PNAs V–VIII which covered both the template and 3' distal regions of the RNA component of telomerase did not yield increased inhibition of telomerase. Indeed, the longest PNA, VIII, which was twenty nucleotides long, inhibited telomerase with an $IC_{50}$ value of 200 nM. Presumably, additional bases of the longer PNA offer more potential for nonspecific contacts in the extract or yield stronger intramolecular secondary structure, thereby reducing the likelihood of binding the telomerase target. Extension of PNAs to cover both the template and the 5' proximal region, PNAs IX, X, XI, XII, and XIII inhibited telomerase activity at $IC_{50}$ values in the range of 10 nM, with one exception, PNA XII, the best inhibitor to be identified in these studies, which possessed an $IC_{50}$ value of 0.9 nM (Table I, FIG. 3). PNAs XIV and XV, which lacked complementarity to hTR, did not detectably inhibit human telomerase activity (Table I). PNAs continued to inhibit telomerase activity with $IC_{50}$ values only slightly higher than those determined for inhibition within purified extracts at 37° C. Table 1 shows the nucleobase sequences of the respective PNA and PS polymers.

TABLE 1

$IC_{50}$ Values for the inhibition of telomerase activity by PNA and PS oligomers

| | | $IC_{50}$ (nM) | | | |
| --- | --- | --- | --- | --- | --- |
| | | Cell Extract | | Perm. Cells | SEQ |
| | Sequence | 25° C. | 37° C. | 37° C. | ID NO: |
| RNA STRAND | 3'-GGGAAGAGUCAAUCCCAAUCUGUUU-5' | | | | 36 |
| | Complementary PNA Sequence | | | | |
| PNA (I) | NH$_2$-GGTTAG-COOH | 30,000 | | | 5 |
| PNA (II) | TAGGGTTAG | 1,000 | | | 20 |
| PNA (III) | TTAGGGTTAG | 200 | 400 | 500 | 8 |
| PNA (IV) | GTTAGGGTTAG | 10 | 100 | 300 | 9 |
| PNA (V) | AGTTAGGGTTAG | 10 | 75 | 370 | 10 |
| PNA (VI) | CAGTTAGGGTTAG | 10 | 50 | 75 | 11 |
| PNA (VII) | CTCAGTTAGGGTTAG | 10 | 70 | 100 | 12 |
| PNA (VIII) | CCCTTCTCAGTTAGGGTTAG | 200 | 300 | 400 | 13 |
| PNA (IX) | TAGGGTTAGAC | 10 | | | 14 |
| PNA (X) | GTTAGGGTTAGAC | 10 | | | 15 |
| PNA (XI) | GGGTTAGACAA | 10 | 50 | 70 | 16 |
| PNA (XII) | TAGGGTTAGACAA | 0.9 | 5 | 50 | 17 |
| PNA (XIII) | GTTAGGGTTAGACAA | 10 | 50 | 100 | 18 |
| | Non-Complementary PNA Sequence | | | | |
| PNA (XIV) | AGGATCTTCACCTAGATCCT | N/D | N/D | | 37 |
| PNA (XV) | TGTAAGGAACTAG | N/D | N/D | | 38 |
| | Complementary PS Sequence | | | | |
| PS (I) | 5'-GTTAGGGTTAG-3' | 75 | 250 | | 39 |
| PS (II) | CTCAGTTAGGGTTAG | 100 | 700 | | 40 |
| PS (III) | TAGGGTTAGACAA | 50 | 200 | | 41 |
| | Non Complementary PS Sequence | | | | |
| PS (IV) | AGGATCTTCACCTAGATCCT | 100 | 400 | | 42 |
| PS (V) | TGTAAGGAACTAG | 100 | 450 | | 43 |

N/D; no inhibition detected at 33 µM PNA concentration.

Figure 4:
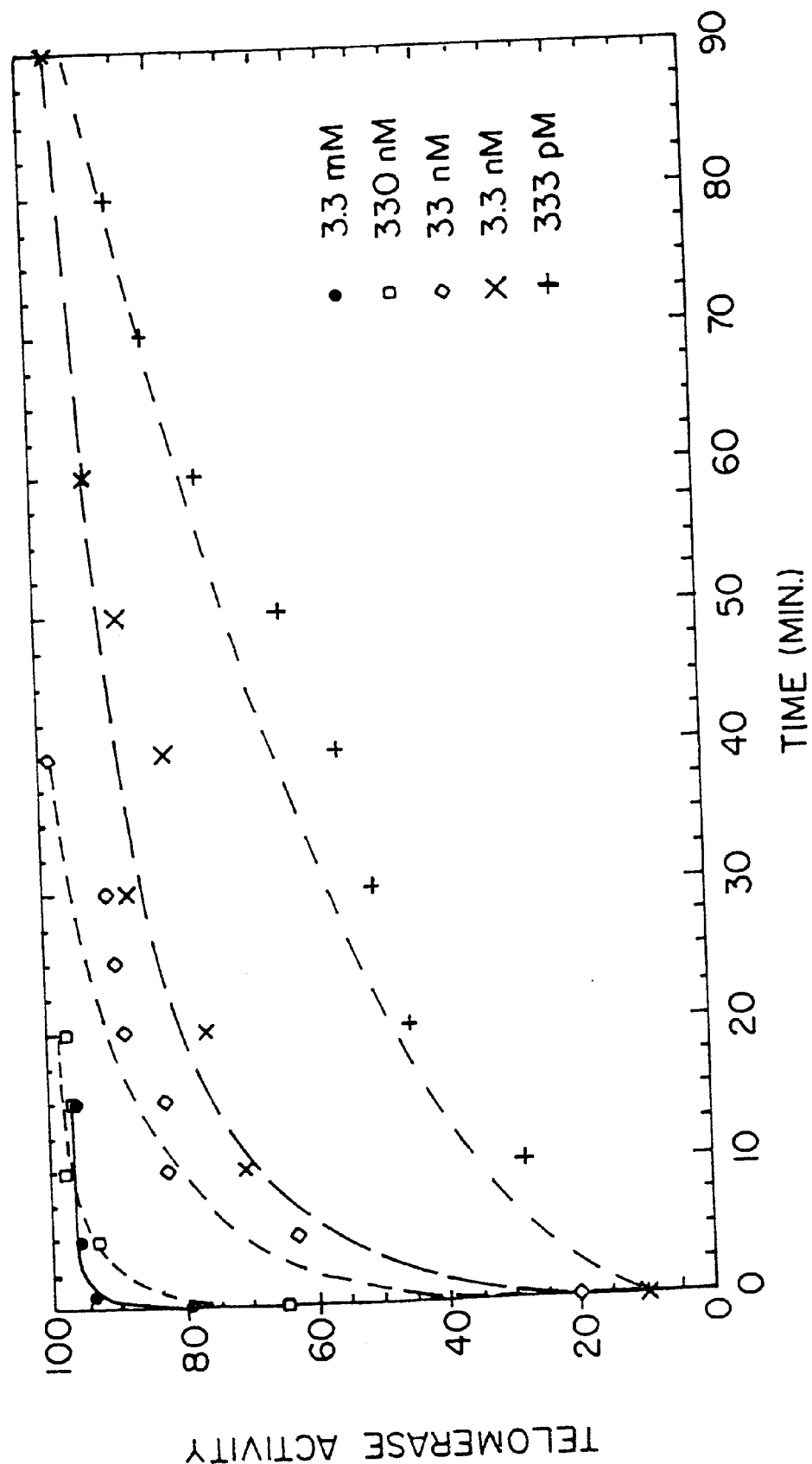
FIG. 4. Inhibition of telomerase as a function of PNA XII concentration and the time allowed for incubation of the PNA with telomerase.

Inhibition of Telomerase as a Function of PNA Concentration and Time—Inhibition was dependent on the concentration of PNA and the time allowed for preincubation with cell extracts containing telomerase (FIG. 4). The presence of 200 nM PNA XII allowed maximal inhibition to be reached after a five minute preincubation of PNA and telomerase. A 300 pM concentration of PNA XII, by contrast, required ninety minutes to achieve maximal inhibition. Once maximal inhibition was attained, it was effectively irreversible.

Lengthy incubations of inhibited telomerase with primer and nucleotides under optimal conditions failed to generate elongated products.

Figure 5:
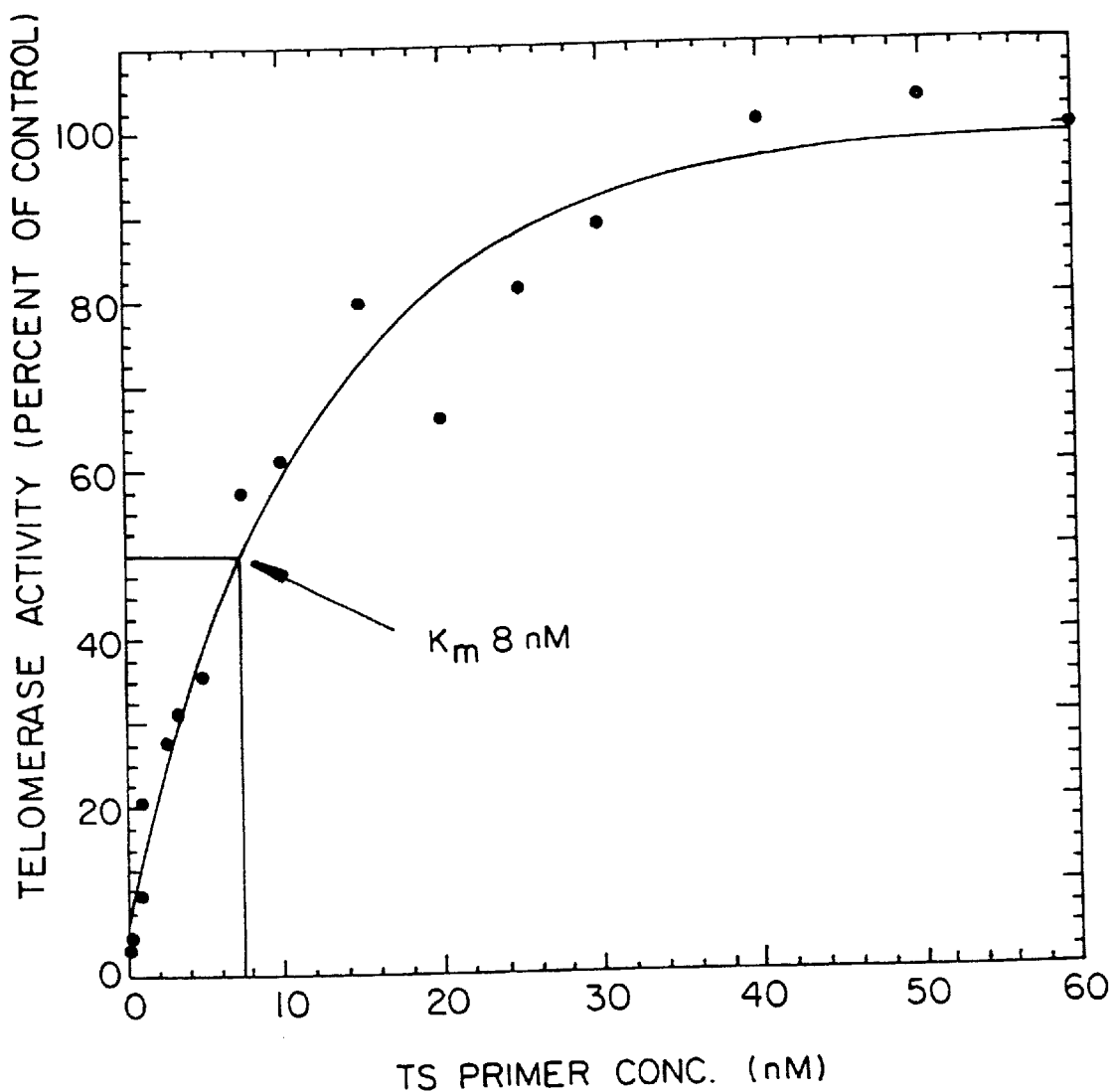
FIG. 5. Determination of Km (apparent) of telomerase for the TS primer. Telomerase assays and quantitations were performed essentially as described, infra. The concentration of TS primer was varied from 0 to 60 nM in the reaction mixture. The reaction was allowed to proceed for 30 minutes at 25° C. followed by amplification as described below. The products were quantitated as described with telomerase activity plotted as a function of the concentration of TS primer.

Binding of TS Primer to Telomerase—To put the efficiency of inhibition into context, the affinity of the TS primer for telomerase was determined. Primer affinity of telomerase was determined by monitoring the level of telomerase activity as a function of concentration of the TS primer. The TS primer is complementary to only three bases of the RNA template of the hTR, and was not initially expected to bind tightly to telomerase. The TRAP assay was performed as described, except that the concentration of the TS primer above the wax barrier was varied from 0 to 60 nM. The concentration of TS primer below the wax barrier was varied to keep the total concentration constant. Surprisingly, however, we observed an apparent binding constant, $K_{m\ app}$, of 8 nM (FIG. 5). The high affinity suggests that interactions between telomerase and DNA primers are not limited to basepairing, and that there are additional interactions involving either the phosphate backbone or unpaired nucleotide bases of the primer.

Inhibition of Telomerase Activity in Permeabilized Cells—Relative to DNA, PNAs possess hydrophobic backbones which may increase interactions with hydrophobic proteins or membranes and non-sequence selective association with RNA or chromosomal DNA. The potential for such interactions to interfere with the location of hTR by PNAs was evaluated by examining elongation under conditions more similar to those in vivo. PNAs were applied to HME50-5 cells that had been mildly permeabilized. Permeabilization facilitates PNA entry into cells, while the retention of telomerase inside cells requires that successful targeting of the RNA template of hTR occur in spite of the high concentrations of endogenous macromolecules. Incubations were performed at 37° C. to further mimic physiologic conditions. Greater than eighty percent of telomerase activity was determined to reside within cells after permeabilization. PNAs continued to inhibit telomerase activity with $IC_{50}$ values only slightly higher than those determined for inhibition within purified extracts at 37° C. (Table I).

Figure 6:
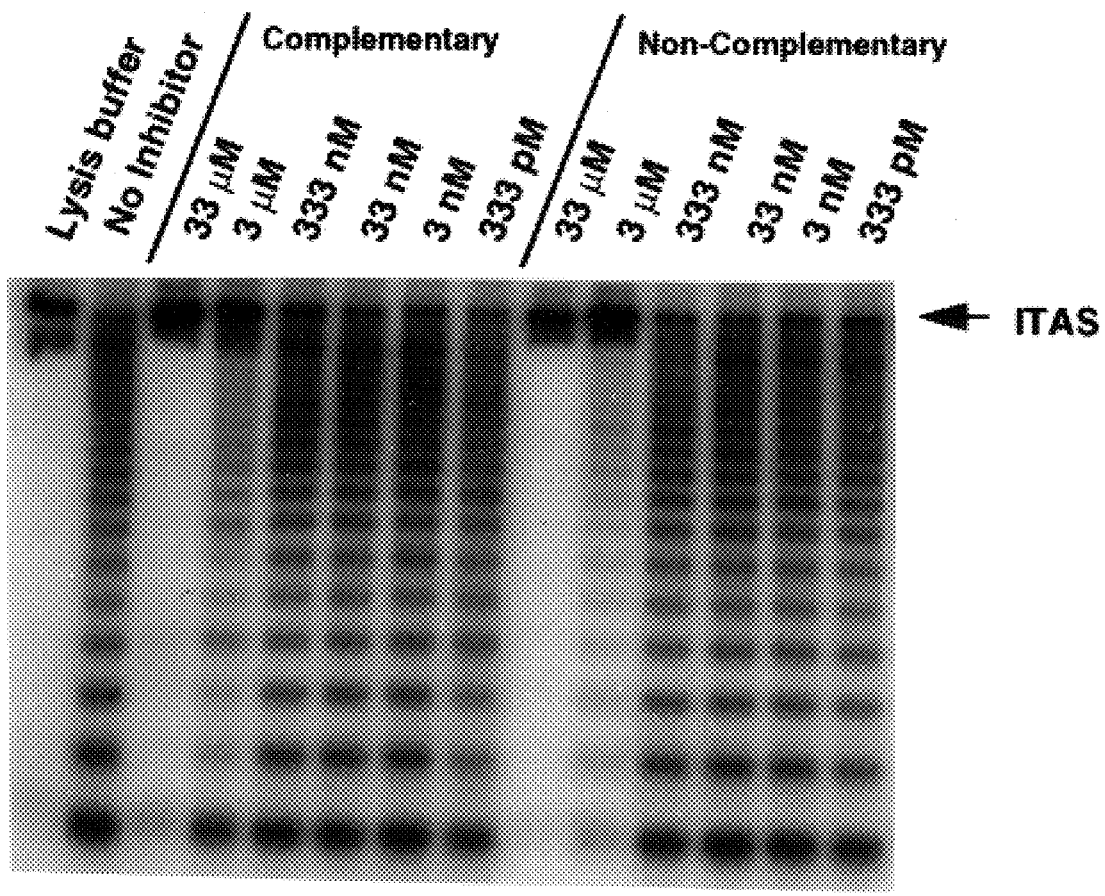
FIG. 6. Inhibition of telomerase activity by varied concentrations of complementary sequence PS oligonucleotide III, and inhibition of telomerase activity by varied concentrations of non-complementary sequence PS oligonucleotide V.

Inhibition of Telomerase Activity by PS oligonucleotides—The relative efficiency of inhibition of telomerase activity by PNAs was put into context by comparison to inhibition by analogous phosphorothioate (PS) oligonucleotides. PS oligonucleotides were synthesized to be analogous in sequence to PNA XII, the most effective PNA inhibitor, and to other PNAs (Table I). We observed that PS oligomers were inhibitors of telomerase activity (FIG. 6, panel A), although inhibition was not as potent as that for PNAs. For example, PS oligonucleotide III inhibited telomerase with an $IC_{50}$ of 50 nM, demonstrating a substantially lower inhibitory effect than that observed for its PNA homologue XII, which exhibited an $IC_{50}$ Of 0.9 nM. Other PS oligomers that were also complementary to hTR were also inhibitors, although their ability to inhibit telomerase activity was less than that of their PNA homologues. However, by contrast to the high selectivity of inhibition by PNAs, which must possess complementarity to hTR to inhibit telomerase activity, PS oligonucleotides that had no complementarity to hTR also inhibited telomerase (FIG. 6, panel B). $IC_{50}$ values for the inhibition of telomerase activity by noncomplementary PS oligonucleotides were almost as potent as those observed for PS oligonucleotides that were complementary (Table I). Neither PS oligonucleotide IV or V possess the ability to form G-quartet structures, indicating that formation of this motif is not necessary to block telomerase activity.

Most previous studies on the inhibition of protein function by oligonucleotides have utilized hybridization to mRNA to limit activity by preventing protein expression. Oligonucleotides, however, can also make specific hydrophobic, electrostatic, and Van der Waals contacts with proteins and thereby inhibit protein function directly. Ribonucleoproteins, macromolecules which consist of both RNA and protein, are a class of targets which we have shown can be inhibited by non-nucleotide polymers capable of interacting with a polynucleotide component in a sequence-dependent manner.

The data disclosed herein demonstrates inhibition of the enzymatic activity of a ribonucleoprotein, telomerase, through hybridization of complementary oligonucleotides to its RNA component in a sequence-dependent manner. The sequence of the RNA template of human telomerase (hTR) has been determined (Feng et al. (1995) op.cit), affording the sequence information necessary to guide the design of additional non-nucleotide oligomer-based inhibitors of the invention. The development of oligomer-based inhibitors of telomerase is especially attractive relative to other knowledge based approaches to inhibitor design, as neither the three dimensional structure of telomerase nor the primary sequence of its protein component are currently known in the art.

This example shows that PNAs, in spite of their inability to participate in backbone-based electrostatic interactions, bind to and effectively inhibit telomerase, and do so with $IC_{50}$ values as low as 0.9 nM. This efficient inhibition contrasts sharply with observations indicating that PNAs cannot inhibit SP6 or T7 RNA polymerase. RNA polymerases can only interact with nucleic acids through sequence selective binding between protein and inhibitory nucleic acid. The lack of an ability to form electrostatic interactions is not, however, an obstacle for inhibition of telomerase by PNAs, consistent with a model wherein Watson-Crick pairing of PNAs with hTR is sufficient for efficient inhibition.

The finding that PNAs complementary to hTR inhibit telomerase at concentrations as low as 0.3 nM and, conversely, that PNAs lacking sequence complementarity do not detectably inhibit, demonstrates that association of PNAs with telomerase can be stable, efficient, and selective. Such compounds might be utilized to probe the intracellular function of telomerase and might be adapted to test the hypothesis that the inhibition of telomerase leads to suppression of tumor growth. Aside from their demonstrated excellent inhibition of telomerase activity, PNAs are well suited as telomerase inhibitors because their high affinity for complementary nucleic acids makes it possible to adapt relatively short PNAs as effective inhibitors. This reduces the cost of inhibitor synthesis and possibly aid bioavailability and membrane permeability. PNA synthesis is based on standard t-boc (Thomson et al. (1995) Tetrahedron 51: 6179, incorporated herein by reference) or f-moc (Wittung et al. (1995) op.cit) based peptide chemistry, facilitating the synthesis of diverse PNA-peptide adducts or PNA-small molecule adducts. Such modifications yield PNA species that can have either increased membrane permeability, increased inhibition, or both. The high affinity of PNA association also indicates that PNAs can be employed as affinity ligands for purification of human telomerase and its associated proteins. The inability of PNAs to bind to proteins that interact with DNA via electrostatic interactions may also increase the specificity of telomerase isolation during purification.

By contrast to the high affinity and selectivity of the inhibition of telomerase activity by PNAS, inhibition by PS oligonucleotides is both less potent and less selective. Unlike the PNA backbone, PS linkages are negatively charged, resulting in electrostatic repulsion between the incoming PS oligonucleotides and the RNA target. PS oligonucleotides have lower melting temperatures for hybridization to complementary sequences than do the corresponding PNAs, and the less stable association probably contributes to the higher $IC_{50}$ values observed for inhibition of telomerase by PS oligonucleotides. Importantly, Watson-Crick pairing is not necessary for inhibition by PS oligonucleotides, as sequences that are not complementary to hTR inhibit telomerase activity with $IC_{50}$ values that are similar to those obtained through addition of complementary PS oligomers.

The observation that PS oligonucleotides inhibit telomerase activity nonselectively is consistent with a model wherein they possess a high affinity for either the protein component of telomerase or for non-template RNA and that this affinity does not depend on the nucleotide sequence of the PS oligomer. The finding that the TS primer possesses strong affinity for telomerase in spite of having only three bases complementary to hTR suggests that nucleic acids can take advantage of non-template interactions to increase binding, and the nonspecific binding of PS oligonucleotides may mimic these interactions to generate stable association in the absence of base-pairing. T7 and SP6 RNA polymerase, reverse transcriptase, and other proteins also bind PS oligonucleotides nonsequence-specifically, indicating that non-selective binding is a general disadvantage of PS oligonucleotides.

The data indicates that PNAs inhibit the activity of human telomerase with high affinity and selectivity. Coupled with studies of the inhibition of SP6 and T7 RNAP by oligonucleotides it is clear that chemical modifications can substantially influence the ability of oligonucleotides to selectively inhibit enzyme activity. The selectivity of PNAs relative to PS oligonucleotides suggests that PNAs or other nonionic oligonucleotides may have important advantages for the recognition of complementary targets within complex cellular environments.

The foregoing examples describe various aspects of the invention and how certain compounds of the invention were made. The examples are not intended to provide an exhaustive description of the many different embodiments of the invention encompassed by the following claims.

We claim:

1. A peptide nucleic acid polymer wherein the nucleobase sequence of the peptide nucleic acid polymer is selected from the group consisting of:

| | |
|---|---|
| —TTAGGGTTAG— | (SEQ ID NO:8); |
| —GTTAGGGTTAG— | (SEQ ID NO:9); |
| —AGTTAGGGTTAG— | (SEQ ID NO:10); |
| —CAGTTAGGGTTAG— | (SEQ ID NO:11); |
| —CTCAGTTAGGGTTAG— | (SEQ ID NO:12); |
| —CCCTTCTCAGTTAGGGTTAG— | (SEQ ID NO:13); |
| —TAGGGTTAGAC— | (SEQ ID NO:14); |
| —GTTAGGGTTAGAC— | (SEQ ID NO: 15); |
| —GGGTTAGACAA— | (SEQ ID NO:16); |
| —TAGGGTTAGACAA— | (SEQ ID NO:17), |
| —GTTAGGGTTAGACAA— | (SEQ IN NO: 18); |
| —TAGGGTTAG— | (SEQ ID NO:20), | and these nucleobase sequences wherein the nucleobase thymine is replaced by the nucleobase uridine, at some or all occurrences of T.

2. A composition comprising a peptide nucleic acid polymer of claim 1 and an excipient or liposome delivery complex.

3. The peptide nucleic acid polymer of claim 1, further comprising from 1 to 10,000 covalently linked nucleotides.

4. The peptide nucleic acid polymer of claim 1, wherein the peptide nucleic acid polymer is covalently linked to a polypeptide sequence that enhances cellular uptake of the peptide nucleic acid polymer, the polypeptide sequence selected from the group consisting of an 11 amino acid peptide of tat, amino acids 84–103 of p16, or a subsequence of a 60 amino acid homeodomain of Antennapedia.

5. A method for modulating mammalian telomerase activity in a cell, the method comprising the step of administering to a mammalian cell in vitro, under conditions where telomerase activity is modulated, a peptide nucleic acid polymer wherein the nucleobase sequence of the peptide nucleic acid polymer is selected from the group consisting of:

| | |
|---|---|
| NH2—TAGGGTTAG—COOH | (SEQ ID NO:20); |
| NH2—TTAGGGTTAG—COOH | (SEQ ID NO:8); |
| NH2—GTTAGGGTTAG—COOH | (SEQ ID NO:9); |
| NH2—AGTTAGGGTTAG—COOH | (SEQ ID NO:10); |
| NH2—CAGTTAGGGTTAG—COOH | (SEQ ID NO:11); |
| NH2—CTCAGTTAGGGTTAG—COOH | (SEQ ID NO: 12); |
| NH2—CCCTTCTCAGTTAGGGTTAG—COOH | (SEQ ID NO: 13); |
| NH2—TAGGGTTAGAC—COOH | (SEQ ID NO: 14); |
| NH2—GTTAGGGTTAGAC—COOH | (SEQ NO:15); |
| NH2—GGGTTAGACAA—COOH | (SEQ D NO:16); |
| NH2—TAGGGTTAGACAA—COOH | (SEQ ID NO:17); |
| NH2—GTTAGGGTTAGACAA—COOH | (SEQ ID NO:18), | and these nucleobase sequences wherein the nucleobase thymine is replaced by the nucleobase uridine, at some or all occurrences of T.

6. The method of claim 5, wherein the cell is a transformed human cell.

7. The method of claim 5, wherein the peptide nucleic acid polymer further comprises from 1 to 10,000 covalently linked nucleotides.

8. The method of claim 5, wherein the peptide nucleic acid polymer is covalently linked to a polypeptide sequence that enhances cellular uptake of the peptide nucleic acid polymer, the polypeptide sequence selected from the group consisting of an 11 amino acid peptide of tat, amino acids 84–103 of p16, or a subsequence of a 60 amino acid homeodomain of Antennapedia.

* * * * *

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "peptide nucleic acid (PNA),
         where (deoxy)ribose-phosphate linkages are replaced by
         N-(2-aminoethyl)glycine units linked to nucleotide bases
         via glycine amino nitrogen through a methylenecarbonyl
         linker"

(xi) SEQUENCE DESCRIPTION: SEQ ID NO:1:

TTAGGG                                                                           6

(2) INFORMATION FOR SEQ ID NO:2:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "peptide nucleic acid (PNA),
         where (deoxy)ribose-phosphate linkages are replaced by
         N-(2-aminoethyl)glycine units linked to nucleotide bases
         via glycine amino nitrogen through a methylenecarbonyl
         linker"

(xi) SEQUENCE DESCRIPTION: SEQ ID NO:2:

TAGGGT                                                                           6

(2) INFORMATION FOR SEQ ID NO:3:

-continued (i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:3:

AGGGTT                                                                6

(2) INFORMATION FOR SEQ ID NO:4:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:4:

GGGTTA                                                                6

(2) INFORMATION FOR SEQ ID NO:5:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:5:

GGTTAG                                                                6

(2) INFORMATION FOR SEQ ID NO:6:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:6:

GTTAGG                                                                6

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:7:

GGTCTTAGGG ACTG                                                          14

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:8:

TTAGGGTTAG                                                               10

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:9:

GTTAGGGTTA G                                                             11

(2) INFORMATION FOR SEQ ID NO:10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:10:

AGTTAGGGTT AG                                                            12

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:11:

CAGTTAGGGT TAG                                                        13

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:12:

CTCAGTTAGG GTTAG                                                      15

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:13:

CCCTTCTCAG TTAGGGTTAG                                                 20

(2) INFORMATION FOR SEQ ID NO:14:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:14:

TAGGGTTAGA C                                                          11

(2) INFORMATION FOR SEQ ID NO:15:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "peptide nucleic acid (PNA),
                  where (deoxy)ribose-phosphate linkages are replaced by
                  N-(2-aminoethyl)glycine units linked to nucleotide bases
                  via glycine amino nitrogen through a methylenecarbonyl
                  linker"

(xi) SEQUENCE DESCRIPTION: SEQ ID NO:15:

GTTAGGGTTA GAC                                                                13

(2) INFORMATION FOR SEQ ID NO:16:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "peptide nucleic acid (PNA),
                  where (deoxy)ribose-phosphate linkages are replaced by
                  N-(2-aminoethyl)glycine units linked to nucleotide bases
                  via glycine amino nitrogen through a methylenecarbonyl
                  linker"

(xi) SEQUENCE DESCRIPTION: SEQ ID NO:16:

GGGTTAGACA A                                                                  11

(2) INFORMATION FOR SEQ ID NO:17:

(i) SEQUENCE CHARACTERISTICS:
              (A) LENGTH: 13 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "peptide nucleic acid (PNA),
                  where (deoxy)ribose-phosphate linkages are replaced by
                  N-(2-aminoethyl)glycine units linked to nucleotide bases
                  via glycine amino nitrogen through a methylenecarbonyl
                  linker"

(xi) SEQUENCE DESCRIPTION: SEQ ID NO:17:

TAGGGTTAGA CAA                                                                13

(2) INFORMATION FOR SEQ ID NO:18:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "peptide nucleic acid (PNA),
                  where (deoxy)ribose-phosphate linkages are replaced by
                  N-(2-aminoethyl)glycine units linked to nucleotide bases
                  via glycine amino nitrogen through a methylenecarbonyl
                  linker"

(xi) SEQUENCE DESCRIPTION: SEQ ID NO:18:

GTTAGGGTTA GACAA                                                              15

(2) INFORMATION FOR SEQ ID NO:19:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:19:

GGUUAG                                                                        6

(2) INFORMATION FOR SEQ ID NO:20:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:20:

TAGGGTTAG                                                                     9

(2) INFORMATION FOR SEQ ID NO:21:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:21:

GGTC                                                                          4

(2) INFORMATION FOR SEQ ID NO:22:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:22:

ACTG                                                                          4

(2) INFORMATION FOR SEQ ID NO:23:

(i) SEQUENCE CHARACTERISTICS:
    (A) LENGTH: 5 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:23:

TATAC                                                                    5

(2) INFORMATION FOR SEQ ID NO:24:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GTATA                                                                    5

(2) INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:25:

CCCTTCTCAG TTAG                                                         14

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:26:

UUUGUCUAAC CCUAACUGAG AAGGG                                             25

(2) INFORMATION FOR SEQ ID NO:27:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:27:

GTATTAGGG                                                                  9

(2) INFORMATION FOR SEQ ID NO:28:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:28:

CAGTATTAGG G                                                              11

(2) INFORMATION FOR SEQ ID NO:29:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:29:

CTCAGTATTA GGG                                                            13

(2) INFORMATION FOR SEQ ID NO:30:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:30:

CUAACCCUAA C                                                              11

(2) INFORMATION FOR SEQ ID NO:31:

(i) SEQUENCE CHARACTERISTICS:
        (A) LENGTH: 486 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:31:

GGGUUGCGGA GGGUGGGCCU GGGAGGGGUG GUGGCCAUUU UUUGUCUAAC CCUAACUGAG          60

AAGGGCGUAG GCGCCGUGCU UUUGCUCCCC GCGCGCUGUU UUUCUCGCUG ACUUUCAGCG         120

GGCGGAAAAG CCUCGGCCUG CCGCCUUCCA CCGUUCAUUC UAGAGCAAAC AAAAAAUGUC         180

AGCUGCUGGC CGUUCGCCC CUCCCGGGGA CCUGCGGCGG GUCGCCUGCC CAGCCCCCGA          240

ACCCCGCCUG GAGGCCGCGG UCGGCCCGGG GCUUCUCCGG AGGCACCCAC UGCCACCGCG         300

-continued

```
AAGAGUUGGG CUCUGUCAGC CGCGGGUCUC UCGGGGGCGA GGGCGAGGUU CAGGCCUUUC      360

AGGCCGCAGG AAGAGGAACG GAGCGAGUCC CCGCGCGCGG CGCGAUUCCC UGAGCUGUGG      420

GACGUGCACC CAGGACUCGG CUCACACAUG CAGUUCGCUU UCCUGUUGGU GGGGGGAACG      480

CCGAUC                                                                486
```

(2) INFORMATION FOR SEQ ID NO:32:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:32:

```
UCUAACCCUA ACUGAGAAGG GCGUAGGCGC CGUGCUUUUG CUCCCCGCGC GCUGUUUUUC       60

UCGCUGACUU UCAGCGGGCG GAAAAGCCUC GGCCUGCCGC CUUCCACCGU UCAUUCUAGA      120

GCAAACAAAA AAUGUCAGCU GCUGGCCCGU UCGCCCCUCC C                         161
```

(2) INFORMATION FOR SEQ ID NO:33:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

```
TCTAACCCTA ACTGAGAAGG GCGTAGGCGC CGTGCTTTTG CTCCCCGCGC GCTGTTTTTC       60

TCGCTGACTT TCAGCGGGCG GAAAAGCCTC GGCCTGCCGC CTTCCACCGT TCATTCTAGA      120

GCAAACAAAA AATGTCAGCT GCTGGCCCGT TCGCCCCTCC C                         161
```

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..18
        (D) OTHER INFORMATION: /note= "TS primer"

(xi) SEQUENCE DESCRIPTION: SEQ ID NO:34:

```
AATCCGTCGA GCAGAGTT                                                    18
```

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24

(D) OTHER INFORMATION: /note= "CX reverse primer"

(xi) SEQUENCE DESCRIPTION: SEQ ID NO:35:

CCCTTACCCT TACCCTTACC CTAA                                          24

(2) INFORMATION FOR SEQ ID NO:36:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:36:

UUUGUCUAAC CCUAACUGAG AAGGG                                         25

(2) INFORMATION FOR SEQ ID NO:37:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                  where (deoxy)ribose-phosphate linkages are replaced by
                  N-(2-aminoethyl)glycine units linked to nucleotide bases
                  via glycine amino nitrogen through a methylenecarbonyl
                  linker"

(xi) SEQUENCE DESCRIPTION: SEQ ID NO:37:

AGGATCTTCA CCTAGATCCT                                               20

(2) INFORMATION FOR SEQ ID NO:38:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "peptide nucleic acid (PNA),
                  where (deoxy)ribose-phosphate linkages are replaced by
                  N-(2-aminoethyl)glycine units linked to nucleotide bases
                  via glycine amino nitrogen through a methylenecarbonyl
                  linker"

(xi) SEQUENCE DESCRIPTION: SEQ ID NO:38:

TGTAAGGAAC TAG                                                      13

(2) INFORMATION FOR SEQ ID NO:39:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "phosphorothioate (PS) nucleic acid"

(xi) SEQUENCE DESCRIPTION: SEQ ID NO:39:

GTTAGGGTTA G                                                        11

(2) INFORMATION FOR SEQ ID NO:40:

(i) SEQUENCE CHARACTERISTICS:
            (A) LENGTH: 15 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS) nucleic acid"

(xi) SEQUENCE DESCRIPTION: SEQ ID NO:40:

CTCAGTTAGG GTTAG                                                    15

(2) INFORMATION FOR SEQ ID NO:41:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS) nucleic acid"

(xi) SEQUENCE DESCRIPTION: SEQ ID NO:41:

TAGGGTTAGA CAA                                                      13

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS) nucleic acid"

(xi) SEQUENCE DESCRIPTION: SEQ ID NO:42:

AGGATCTTCA CCTAGATCCT                                               20

(2) INFORMATION FOR SEQ ID NO:43:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "phosphorothioate (PS) nucleic acid"

(xi) SEQUENCE DESCRIPTION: SEQ ID NO:43:

TGTAAGGAAC TAG                                                      13

(2) INFORMATION FOR SEQ ID NO:44:

(i) SEQUENCE CHARACTERISTICS:
        (A) LENGTH: 4 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "peptide nucleic acid (PNA),
            where (deoxy)ribose-phosphate linkages are replaced by
            N-(2-aminoethyl)glycine units linked to nucleotide bases
            via glycine amino nitrogen through a methylenecarbonyl
            linker"

(xi) SEQUENCE DESCRIPTION: SEQ ID NO:44:

ACAA                                                                 4

(2) INFORMATION FOR SEQ ID NO:45:
```

```
        (i) SEQUENCE CHARACTERISTICS:
            (A) LENGTH: 5 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:45:

CCAAT                                                                           5

(2) INFORMATION FOR SEQ ID NO:46:

(i) SEQUENCE CHARACTERISTICS:
            (A) LENGTH: 4 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:46:

TATA                                                                            4
```